(12) United States Patent
Bernard et al.

(10) Patent No.: US 9,861,560 B2
(45) Date of Patent: Jan. 9, 2018

(54) COSMETIC COMPOSITION

(71) Applicant: L'OREAL, Paris (FR)

(72) Inventors: Anne-Laure Bernard, Tokyo (JP); Jinglan Li, Kanagawa (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/653,305

(22) PCT Filed: Dec. 20, 2013

(86) PCT No.: PCT/JP2013/085302
§ 371 (c)(1),
(2) Date: Jun. 18, 2015

(87) PCT Pub. No.: WO2014/098265
PCT Pub. Date: Jun. 26, 2014

(65) Prior Publication Data
US 2015/0335538 A1 Nov. 26, 2015

(30) Foreign Application Priority Data
Dec. 21, 2012 (JP) ................................. 2012-280294

(51) Int. Cl.
| | | |
|---|---|---|
| *A61K 8/06* | (2006.01) | |
| *A61K 8/31* | (2006.01) | |
| *A61K 8/39* | (2006.01) | |
| *A61K 8/92* | (2006.01) | |
| *A61K 8/60* | (2006.01) | |
| *A61Q 1/00* | (2006.01) | |
| *A61Q 5/00* | (2006.01) | |
| *A61Q 19/00* | (2006.01) | |
| *A61Q 19/10* | (2006.01) | |
| *A61Q 1/14* | (2006.01) | |
| *A61Q 5/02* | (2006.01) | |

(52) U.S. Cl.
CPC .............. *A61K 8/062* (2013.01); *A61K 8/31* (2013.01); *A61K 8/39* (2013.01); *A61K 8/604* (2013.01); *A61K 8/92* (2013.01); *A61Q 1/00* (2013.01); *A61Q 1/14* (2013.01); *A61Q 5/002* (2013.01); *A61Q 19/00* (2013.01); *A61Q 19/10* (2013.01); *A61K 2800/10* (2013.01); *A61K 2800/262* (2013.01); *A61K 2800/596* (2013.01); *A61Q 5/02* (2013.01)

(58) Field of Classification Search
CPC .......... A61K 2800/10; A61K 2800/262; A61K 2800/596; A61K 8/062; A61K 8/31; A61K 8/39; A61K 8/604; A61K 8/92; A61Q 19/00; A61Q 19/10; A61Q 1/00; A61Q 1/14; A61Q 5/002; A61Q 5/02
See application file for complete search history.

(56) References Cited

U.S. PATENT DOCUMENTS

| | | |
|---|---|---|
| 2,528,378 A | 10/1950 | Mannheimer |
| 2,781,354 A | 2/1957 | Mannheimer |
| 2,798,053 A | 7/1957 | Brown |
| 2,923,692 A | 2/1960 | Ackerman et al. |
| 3,915,921 A | 10/1975 | Schlatzer, Jr. |
| 4,137,180 A | 1/1979 | Naik et al. |
| 4,237,243 A | 12/1980 | Quack et al. |
| 4,509,949 A | 4/1985 | Huang et al. |
| 4,874,554 A | 10/1989 | Lange et al. |
| 5,364,633 A | 11/1994 | Hill et al. |
| 5,411,744 A | 5/1995 | Hill et al. |
| 7,452,917 B2 | 11/2008 | Baumoeller et al. |
| 7,829,106 B2* | 11/2010 | Hiyama ................... A61K 8/39 424/400 |
| 7,879,915 B2 | 2/2011 | Sorns et al. |
| 2003/0206933 A1* | 11/2003 | Schulze zur Wiesche .............. A61K 8/4973 424/401 |
| 2003/0224024 A1 | 12/2003 | Leveque et al. |
| 2004/0116542 A1 | 6/2004 | Baumoeller et al. |
| 2004/0209795 A1* | 10/2004 | Vlad ....................... A61K 8/062 512/4 |
| 2006/0078525 A1 | 4/2006 | Tomokuni |
| 2006/0167102 A1 | 7/2006 | Leveque et al. |
| 2008/0031907 A1* | 2/2008 | Tamarkin ............... A61K 8/046 424/401 |
| 2010/0068307 A1* | 3/2010 | Nielloud ................ A61K 8/042 424/702 |
| 2010/0242796 A1 | 9/2010 | Sorns et al. |

FOREIGN PATENT DOCUMENTS

| | | |
|---|---|---|
| EP | 0216479 A1 | 4/1987 |
| EP | 1333022 A2 | 8/2003 |
| FR | 2416723 A1 | 9/1979 |
| JP | H09-110635 A | 4/1997 |
| JP | H11-71256 A | 3/1999 |
| JP | 2006-117643 A | 5/2006 |

(Continued)

OTHER PUBLICATIONS

Janben et al.—Full English Translation of WO 2010/060896 A1, Jun. 3, 2010, pp. 1-83.*

(Continued)

*Primary Examiner* — Aradhana Sasan
(74) *Attorney, Agent, or Firm* — The Marbury Law Group, PLLC

(57) ABSTRACT

The present invention relates to a cosmetic composition in the form of a nano- or micro-emulsion, comprising: (a) at least one oil; (b) at least one polyglyceryl fatty acid ester, preferably with a polyglyceryl moiety derived from 3 to 6 glycerins, and more preferably 5 or 6 glycerins; (c) at least one alkyl (poly)glucoside type surfactant; (d) at least one amphoteric surfactant; and (e) water. The cosmetic composition according to the present invention has a dispersed phase which has a smaller diameter due to a combination of the (b) polyglyceryl fatty acid ester and the (c) alkyl (poly) glucoside type surfactant, and the (d) amphoteric surfactant. Therefore, the cosmetic composition can be in the form of a nano- or micro-emulsion with a transparent or slightly translucent aspect.

20 Claims, No Drawings

(56) References Cited

FOREIGN PATENT DOCUMENTS

| JP | 2007-320884 A | 12/2007 | | |
|---|---|---|---|---|
| JP | 2010-254624 A | 11/2010 | | |
| WO | 00/61083 A1 | 10/2000 | | |
| WO | 02/056841 A2 | 7/2002 | | |
| WO | 2008/067944 A1 | 6/2008 | | |
| WO | 2010/060896 A1 | 6/2010 | | |
| WO | WO 2010/060896 A1 * | 6/2010 | ............... | A61K 8/04 |
| WO | 2014/098264 A1 | 6/2014 | | |

OTHER PUBLICATIONS

International Search Report and Written Opinion for PCT/JP2013/085301, dated Apr. 8, 2014.
International Search Report and Written Opinion for PCT/JP2013/085302, dated Apr. 8, 2014.
Meylan, W.M., et al., "Atom/Fragment Contribution Method for Estimating Octanol-Water Partition Coefficients," Journal of Pharmaceutical Sciences, vol. 84, No. 1, Jan. 1995, pp. 82-93.
Todd, Charles, et al., "Volatile Silicone Fluids for Cosmetic Formulations," Cosmetics and Toiletries, vol. 91, Jan. 1976, pp. 29-32.
Griffin, William C., "Calculation of HLB Values of Non-Ionic Surfactants," J. Soc. Cosmet. Chemists, vol. 5 (1954), pp. 249-256.
MacGregor, E.A., et al., "Polymers in Nature," Chapter 6, 1980, pp. 240-328.
Kirk-Othmer, Encyclopedia of Chemical Technology, 3rd Ed., vol. 15, 1982, pp. 439-458.
Shinoda et al., "The Stability of O/W Type Emulsions as Functions of Temperature and the HLB of Emulsifiers: The Emulsification by PIT-Method," Journal of Colloid and Interface Science, vol. 30, No. 2, Jun. 1969, pp. 258-263.
Mitsui et al., "Application of the Phase-Inversion-Temperature Method to the Emulsification of Cosmetics," American Cosmetics and Perfumery, vol. 87, Dec. 1972, pp. 33-36.
English language abstract for JPH 09-110635A (Apr. 28, 1997).
English language abstract for JPH 11-71256A (Mar. 16, 1999.
English language abstract for WO 2010/060896A1 (Jun. 3, 2010).
Japanese Office Action for counterpart JP Application No. 2012-280294, dated Nov. 7, 2016 (with English Translation).

\* cited by examiner

COSMETIC COMPOSITION

CROSS REFERENCE TO RELATED APPLICATION

This is a national stage application of PCT/JP2013/085302, filed internationally on Dec. 20, 2013, which claims priority Japanese Application No. 2012-280294, filed on Dec. 21, 2012, both of which are incorporated herein by reference in their entireties.

TECHNICAL FIELD

The present invention relates to a foaming composition in the form of a nano- or micro-emulsion.

BACKGROUND ART

Oil-in-water (O/W) or Water-in-oil (W/O) emulsions are well known in the field of cosmetics and dermatology, in particular for the preparation of cosmetic products, such as milks, creams, tonics, serums or toilet waters. In particular, a fine emulsion such as an O/W nano- or micro-emulsion is particularly interesting in cosmetic products due to its transparent or slightly translucent aspect.

For example, JP-A-H09-110635 discloses a fine emulsion which is formed by using a combination of polyglyceryl fatty acid ester, as a surfactant, and $C_{10}$-$C_{22}$ 2-hydroxy fatty acid. In addition, JP-A-H11-71256 discloses a fine emulsion which is formed by using a combination of polyglyceryl fatty acid ester and a betain.

DISCLOSURE OF INVENTION

There is some interest to introduce oil into foaming cleansers to improve cleansing thanks to the oil detergency potential—There is also some interest to introduce oil into foaming cleansers if the latter has some conditioning potential.

The solubilization of oil in a foaming cleanser remains difficult. For this purpose, it is common to add to foaming surfactant a non ionic surfactant to ease solubilization of oil.

However, when a certain type of a nonionic surfactant is used for preparing a fine emulsion such as a nano- or micro-emulsion, the transparent or slightly translucent aspect of the emulsion as well as stability of the emulsion, are impaired. Furthermore, the quality of foam formed by the emulsion tends to be impaired.

An objective of the present invention is to provide a stable cosmetic composition in the form of a nano- or micro-emulsion with transparent or slightly translucent, preferably transparent, aspect of the emulsion, and better foam quality, even when the above nonionic surfactant is used.

The above objective of the present invention can be achieved by a foaming composition in the form of a nano or micro-emulsion comprising:
(a) at least one oil;
(b) at least one polyglyceryl fatty acid ester, with preferably an HLB value from 8.0 to 13.0, preferably from 9.0 to 13.0, and more preferably from 10.0 to 13.0;
(c) at least one $C_{6-30}$, preferably $C_{12-30}$, alkyl(poly)glucoside type surfactant;
(d) at least one amphoteric surfactant; and
(e) water.

The (a) oil may be selected from the group consisting of oils of plant or animal origin, synthetic oils, silicone oils and hydrocarbon oils. Preferably, the (a) oil may be chosen from hydrocarbon oils which are in the form of a liquid at a room temperature. It may be preferable that the (a) oil be chosen from oils with molecular weight below 600 g/mol.

The amount of the (a) oil may range from 0.1 to 30% by weight, preferably from 0.5 to 25% by weight, and more preferably from 1 to 20% by weight, relative to the total weight of the composition.

The (b) polyglyceryl fatty acid ester may have an HLB value of from 8.0 to 14.0, preferably from 9.0 to 13.5, and more preferably from 10.0 to 13.0.

The (b) polyglyceryl fatty acid ester may have a polyglyceryl moiety derived from 2-10 glycerins, preferably between 3-6, more preferably 4-6, and even more preferably 5-6.

The (b) polyglyceryl fatty acid ester may be chosen from the mono, di and tri esters of lauric acid, isostearic acid, and oleic acid.

The (b) polyglyceryl fatty acid ester may be selected from the group consisting of PG2 isostearate, PG2 laurate, PG2 caprate, PG-5 laurate, PG-4 laurate, PG-5 oleate, and PG-5 dioleate, PG5 myristate, PG5 trioleate, PG5 stearate, PG5 isostearate, PG5 triisostearate, PG10 trilaurate, PG10 isostearate, PG10 diisostearate, PG10 oleate, PG10 trioleate, and PG10 triisostearate.

The (b) polyglyceryl fatty acid ester raw material may be chosen from a mixture of polyglyceryl fatty acid esters, preferably with a polyglyceryl moiety derived from 3 to 6 glycerins, more preferably 4 to 6 glycerins, wherein the mixture preferably comprises at least 30% by weight of a polyglyceryl fatty acid ester with a polyglyceryl moiety consisting of 4, 5 or 6 glycerins.

It is preferable than the (b) polyglyceryl fatty acid ester raw material comprises esters of a fatty acid and polyglycerine containing 70% or more of polyglycerine whose polymerization degree is 4 or more, preferably esters of a fatty acid and polyglycerine containing equal to or more than 60% of polyglycerine whose polymerization degree is between 4 and 11, and more preferably esters of a fatty acid and polyglycerine containing equal to or more than 30% of polyglycerine whose polymerization degree is 5.

The amount of the (b) polyglyceryl fatty acid ester may range from 0.1 to 15% by weight, preferably from 0.5 to 10% by weight, and more preferably from 0.5 to 5% by weight, relative to the total weight of the composition.

The weight ratio of the (b) polyglyceryl fatty acid ester to the (a) oil may be from 0.3 to 6, preferably from 0.4 to 3, and more preferably from 0.5 to 1.5.

The alkyl(poly)glucoside type surfactant may be represented by the formula:

$$R_1O\text{---}(R_2O)_t\text{-}(G)_v$$

wherein $R_1$ represents a linear or branched alkyl and/or alkylene radical comprising from 1 to 30, preferably 6 to 30, and more preferably 12 to 30 carbon atoms or an aralkyl radical, the linear or branched aralkyl radical of which comprises from 7 to 30 carbon atoms, preferably 10 to 30, and more preferably 13 to 30 carbon atoms, $R_2$ represents one or more alkylene radicals comprising approximately from 2 to 4 carbon atoms, G represents a sugar unit comprising from 5 to 6 carbon atoms, t denotes a value ranging from 0 to 10, preferably from 0 to 4, and v denotes a value ranging from 1 to 15, preferably from 1 to 4.

It is preferable that the (c) alkyl(poly)glucoside type surfactant is a $C_{12-30}$ alkyl(poly)glucoside type surfactant except for coco glucoside.

The amount of the alkyl(poly)glucoside type surfactant may range from 0.1 to 25% by weight, preferably from 1 to 20% by weight, and more preferably from 2 to 15% by weight, relative to the total weight of the composition.

The amount of the (d) amphoteric surfactant may range from 0.1 to 25% by weight, preferably from 0.5 to 20% by weight, and more preferably from 1 to 15% by weight, relative to the total weight of the composition.

The cosmetic composition according to the present invention may further comprise at least one anionic surfactant.

The cosmetic composition according to the present invention may further comprise at least one polyol.

The cosmetic composition according to the present invention may further comprise at least one thickening agent, preferably selected from associative thickeners.

It is preferable that the cosmetic composition according to the present invention be in the form of an O/W emulsion, and the (a) oil be in the form of a droplet with a number average particle size of 300 nm or less, preferably from 10 nm to 150 nm.

The transparency may be measured by measuring the nephelometric turbidity (for example, with 2100Q Portable Turbidimeter from HACH).

The cosmetic composition according to the present invention may preferably have a nephelometric turbidity lower than 150 NTU, preferably lower than 100 NTU, and more preferably Lower than 50 NTU.

Further, the present invention also relates to a non-therapeutic process for treating the skin, the hair, mucous membranes, the nails, the eyelashes, the eyebrows and/or the scalp, characterized in that the cosmetic composition according to the present invention is applied to the skin, the hair, mucous membranes, the nails, the eyelashes, the eyebrows or the scalp.

Furthermore, the present invention also relates to a use of the cosmetic composition according to the present invention, as or in care products and/or washing products and/or make-up products and/or make-up-removing products for body and/or facial skin and/or mucous membranes and/or the scalp and/or the hair and/or the nails and/or the eyelashes and/or the eyebrows.

BEST MODE FOR CARRYING OUT THE INVENTION

After diligent research, the inventors have discovered that it is possible to provide a stable cosmetic composition in the form of a nano- or micro-emulsion with transparent or slightly translucent, preferably transparent, aspect of the emulsion, with good foam quality, by using a specific nonionic surfactant.

Thus, the present invention is a cosmetic composition in the form of a foaming composition in the form of a nano or micro-emulsion comprising:
(a) at least one oil;
(b) at least one polyglyceryl fatty acid ester, with preferably an HLB value from 8.0 to 14.0, preferably from 9.0 to 13.5, and more preferably from 10.0 to 13.0;
(c) at least one $C_{6-30}$, preferably $C_{12-30}$, alkyl(poly)glucoside type surfactant;
(d) at least one amphoteric surfactant; and
(e) water.

The cosmetic composition according to the present invention has a dispersed phase which has a smaller diameter due to a combination of the polyglyceryl fatty acid ester, the alkyl(poly)glucoside type surfactant and the amphoteric surfactant. Therefore, the cosmetic composition can be in the form of a nano- or micro-emulsion with transparent or slightly translucent, which can provide superior foam quality.

Since the cosmetic composition according to the present invention can have transparent or slightly translucent, the composition can be preferably used for lotions and the like. Further, as the dispersed phase is finely dispersed, the cosmetic composition according to the present invention can provide unique texture, moisturizing and wet feeling, as well as increased suppleness. Furthermore, if the dispersed phase is an oil phase and includes one or more lipophilic or even amphiphilic active ingredients, the dispersed oil phase can function as a carrier of the active ingredient and accelerate the penetration of the active ingredients into the skin, or can distribute the active ingredients on the skin.

In addition, since the cosmetic composition according to the present invention can have superior foam quality using oils with good cleansing potential, the composition can be preferably used for face cleansing products such as make-up cleansing agents.

Hereinafter, the cosmetic composition according to the present invention will be explained in a more detailed manner.

[Oil]

The cosmetic composition according to the present invention comprises at least one oil. Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile, preferably non-volatile.

The oil may be a non-polar oil such as a hydrocarbon oil, a silicone oil, or the like; a polar oil such as a plant or animal oil and an ester oil; or a mixture thereof.

It is preferable that the (a) oil be selected from the group consisting of oils of plant or animal origin, synthetic oils, silicone oils and hydrocarbon oils.

As examples of plant oils, mention may be made of for example, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of ester oils and artificial triglyceride.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprising in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® EZ 3109 sold by the company Union Carbide, of formula:

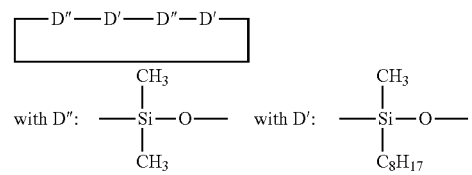

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups are polydiarylsiloxanes, especially polydiphenylsiloxanes and polyalkylarylsiloxanes. Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250 and SF 1265.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as mineral oil (e.g., liquid paraffin), paraffin, vaseline or petrolatum, naphthalenes, and the like; hydrogenated polyisobutene, isoeicosan, and decene/butene copolymer; and mixtures thereof.

It is preferable that the (a) oil be chosen from hydrocarbon oils which are in the form of a liquid at a room temperature.

It is also preferable that the (a) oil be chosen from oils with molecular weight below 600 g/mol.

Preferably, the (a) oil has a low molecular weight such as below 600 g/mol, chosen among ester oils with a short hydrocarbon chain or chains (e.g., isopropyl myristate, isopropyl palmitate, isononyl isononanoate, dicaprylyl carbonate and ethyl hexyl palmitate), short ether oil such as dicaprylyl ether, hydrocarbon oils with a short alkyl chain or chains (e.g., isododecane, isohexadecane, and squalane), short alcohol type oils such as octyldodecanol.

The amount in the cosmetic composition according to the present invention of the (a) oil is not limited, and may range from 0.1 to 30% by weight, preferably from 0.5 to 25% by weight, and more preferably from 1 to 20% by weight, relative to the total weight of the composition.

[Polyglyceryl Fatty Acid Ester]

The cosmetic composition according to the present invention comprises at least one polyglyceryl fatty acid ester. A single type of polyglyceryl fatty acid ester may be used, but two or more different types of polyglyceryl fatty acid ester may be used in combination.

It is preferable that the (b) polyglyceryl fatty acid ester have a polyglycol moiety derived from 2 to 10 glycols, more preferably from 3 to 6 glycols, and further more preferably 5 or 6 glycols.

The (b) polyglyceryl fatty acid ester may have an HLB (Hydrophilic Lipophilic Balance) value of from 8.0 to 14.0, preferably from 9.0 to 13.5, and more preferably from 10.0 to 13.0. If two or more polyglyceryl fatty acid esters are used, the HLB value is determined by the weight average of the HLB values of all the polyglyceryl fatty acid esters.

The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984).

The term HLB ("hydrophilic-lipophilic balance") is well known to those skilled in the art, and denotes the hydrophilic-lipophilic balance of a surfactant.

The HLB or hydrophilic-lipophilic balance of the surfactant(s) used according to the invention is the HLB according to Griffin, defined in the publication *J. Soc. Cosm. Chem.*, 1954 (Vol 5), pages 249-256 or the HLB determined experimentally and as described in the publication from the authors F. Puisieux and M. Seiller, entitled "Galenica 5: Les systèmes dispersés [Dispersed systems]—Volume I—Agents de surface et émulsions [Surface agents and emulsions]—Chapter IV—Notions de HLB et de HLB critique [Notions of HLB and of critical HLB], pages 153-194—paragraph 1.1.2. Détermination de HLB par voie expérimentale [Experimental determination of HLB], pages 164-180.

It is preferably the calculated HLB values that should be taken into account.

The calculated HLB is defined as being the following coefficient:

calculated HLB=20×molar mass of the hydrophilic part/total molar mass.

For an oxyethylenated fatty alcohol, the hydrophilic part corresponds to the oxyethylene units fused to the fatty alcohol and the calculated HLB then corresponds to the HLB according to Griffin (Griffin W. C., J. Soc. Cosmet. Chemists, 5, 249, 1954).

The (b) polyglyceryl fatty acid ester may be chosen from the mono, di and tri esters of saturated or unsaturated acid, preferably saturated acid, including 2 to 30 carbon atoms, preferably 6 to 30 carbon atoms, and more preferably 8 to 30 carbon atoms, such as lauric acid, oleic acid, stearic acid, isostearic acid, capric acid, caprylic acid, and myristic acid.

The polyglyceryl fatty acid ester may be selected from the group consisting of PG2 caprate, PG2 dicaprate, PG2 tricaprate, PG2 caprylate, PG2 dicaprylate, PG2 tricaprylate, PG2 laurate, PG2 dilaurate, PG2 trilaurate, PG2 myristate, PG2 dimyristate, PG2 trimyristate, PG2 stearate, PG2 distearate, PG2 tristearate, PG2 isostearate, PG2 diisostearate, PG2 triisostearate, PG2 oleate, PG2 dioleate, PG2 trioleate, PG3 caprate, PG3 dicaprate, PG3 tricaprate, PG3 caprylate, PG3 dicaprylate, PG3 tricaprylate, PG3 laurate, PG3 dilaurate, PG3 trilaurate, PG3 myristate, PG3 dimyristate, PG3 trimyristate, PG3 stearate, PG3 distearate, PG3 tristearate, PG3 isostearate, PG3 diisostearate, PG3 triisostearate, PG3 oleate, PG3 dioleate, PG3 trioleate, PG4 caprate, PG4 dicaprate, PG4 tricaprate, PG4 caprylate, PG4 dicaprylate, PG4 tricaprylate, PG4 laurate, PG4 dilaurate, PG4 trilaurate, PG4 myristate, PG4 dimyristate, PG4 trimyristate, PG4 stearate, PG4 distearate, PG4 tristearate, PG4 isostearate, PG4 diisostearate, PG4 triisostearate, PG4 oleate, PG4 dioleate, PG4 trioleate, PG5 caprate, PG5 dicaprate, PG5 tricaprate, PG5 caprylate, PG5 dicaprylate, PG5 tricaprylate, PG5 laurate, PG5 dilaurate, PG5 trilaurate, PG5 myristate, PG5 dimyristate, PG5 trimyristate, PG5 stearate, PG5 distearate, PG5 tristearate, PG5 isostearate, PG5 diisostearate, PG5 triisostearate, PG5 oleate, PG5 dioleate, PG5 trioleate, PG6 caprate, PG6 dicaprate, PG6 tricaprate, PG6 caprylate, PG6 dicaprylate, PG6 tricaprylate, PG6 laurate, PG6 dilaurate, PG6 trilaurate, PG6 myristate, PG6 dimyristate, PG6 trimyristate, PG6 stearate, PG6 distearate, PG6 tristearate, PG6 isostearate, PG6 diisostearate, PG6 triisostearate, PG6 oleate, PG6 dioleate, PG6 trioleate, PG10 caprate, PG10 dicaprate, PG10 tricaprate, PG10 caprylate, PG10 dicaprylate, PG10 tricaprylate, PG10 laurate, PG10 dilaurate, PG10 trilaurate, PG10 myristate, PG10 dimyristate, PG10 trimyristate, PG10 stearate, PG10 distearate, PG10 tristearate, PG10 isostearate, PG10 diisostearate, PG10 triisostearate, PG10 oleate, PG10 dioleate, and PG10 trioleate.

It is preferable that the (b) polyglyceryl fatty acid ester be chosen from:
  polyglyceryl monolaurate comprising 4 to 6 glycerol units,
  polyglyceryl mono(iso)stearate comprising 4 to 6 glycerol units,
  polyglyceryl monooleate comprising 4 to 6 glycerol units, and
  polyglyceryl dioleate comprising 4 to 6 glycerol units.

In one embodiment, the (b) polyglyceryl fatty acid ester raw material may be chosen from a mixture of polyglyceryl fatty acid esters, preferably with a polyglyceryl moiety derived from 4 to 6 glycerins, more preferably 5 or 6 glycerins, wherein the mixture preferably comprises 30% by weight or more of a polyglyceryl fatty acid ester with a polyglyceryl moiety consisting of 4, 5 or 6 glycerins.

It is preferable that the (b) polyglyceryl fatty acid ester raw material comprises esters of a fatty acid and polyglycerine containing 70% or more of polyglycerine whose polymerization degree is 4 or more, preferably esters of a fatty acid and polyglycerine containing equal to or more than 60% of polyglycerine whose polymerization degree is between 4 and 11, and more preferably esters of a fatty acid and polyglycerine containing equal to or more than 30% of polyglycerine whose polymerization degree is 5.

The amount in the cosmetic composition according to the present invention of the (b) polyglyceryl fatty acid ester is not limited, and may range from 0.1 to 15% by weight, preferably from 0.5 to 10% by weight, and more preferably from 0.5 to 5% by weight, relative to the total weight of the composition.

[Alkyl(poly)glucoside]

The cosmetic composition according to the present invention comprises at least one alkyl(poly)glucoside type surfactant. A single type of alkyl(poly)glucoside type surfactant may be used, but two or more different types of alkyl(poly) glucoside type surfactant may be used in combination.

The (c) alkyl(poly)glucoside type surfactant may be represented by the formula:

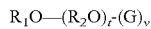

wherein
$R_1$ represents a linear or branched alkyl and/or alkylene radical comprising from 1 to 30, preferably 6 to 30, and more preferably 12 to 30 carbon atoms or an aralkyl radical, the linear or branched aralkyl radical of which comprises from 7 to 30 carbon atoms, preferably 10 to 30, and more preferably 13 to 30 carbon atoms, $R_2$ represents one or more alkylene radicals comprising approximately from 2 to 4 carbon atoms, G represents a sugar unit comprising from 5 to 6 carbon atoms, t denotes a value ranging from 0 to 10, preferably from 0 to 4, and v denotes a value ranging from 1 to 15, preferably from 1 to 4.

The sugar unit containing 5 or 6 carbon atoms represented by G in the above formula may be a reduced sugar selected from the group consisting of glucose, fructose and galactose.

The (c) alkyl(poly)glucoside type surfactant may be selected from the group consisting of caprylyl/capryl glucoside, decyl glucoside, lauryl glucoside, cetearyl glucoside, arachidyl glucoside, isostearyl glucoside, oleyl glucoside and mixtures thereof.

Examples of (c) alkyl(poly)glucoside type surfactant that may be mentioned include decylglucoside (alkyl-$C_9/C_{11}$-polyglucoside (1.4)), for instance the product sold under the name Mydol 10 by the company Kao Chemicals, the product sold under the name Plantaren 2000 UP and Plantacare 2000 UP by the company Henkel, and the product sold under the name Oramix NS 10 by the company SEPPIC; caprylyl/capryl glucoside, for instance the product sold under the name Oramix CG110 by the company SEPPIC or under the name Lutensol GD70 by the company BASF; laurylglucoside, for instance the products sold under the names Plantaren 1200 N and Plantacare 1200 by the company Henkel; and coco-glucoside, for instance the product sold under the name Plantacare 818/UP by the company Henkel, and mixtures thereof.

It is preferable that the (c) alkyl(poly)glucoside type surfactant be a $C_{12-30}$ alkyl(poly)glucoside type surfactant except for coco glucoside.

The amount of the (c) alkyl(poly)glucoside type surfactant is not limited, and may range from 0.1 to 25% by weight, preferably from 1 to 20% by weight, and more preferably from 2 to 15% by weight, relative to the total weight of the composition.

[Amphoteric Surfactant]

The cosmetic composition according to the present invention comprises at least one amphoteric surfactant. A single type of amphoteric surfactant may be used, but two or more different types of amphoteric surfactant may be used in combination.

The (d) amphoteric surfactant is not limited. The amphoteric or zwitterionic surfactants can be, for example (non-limiting list), amine derivatives such as aliphatic secondary or tertiary amine, and optionally quaternized amine derivatives, in which the aliphatic radical is a linear or branched chain comprising 8 to 22 carbon atoms and containing at least one water-solubilizing anionic group (for example, carboxylate, sulphonate, sulphate, phosphate or phosphonate).

Among the amidoaminecarboxylated derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference), under the names Amphocarboxyglycinates and Amphocarboxypropionates, with the respective structures:

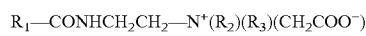

in which:

$R_1$ denotes an alkyl radical of an acid $R_1$—COOH present in hydrolysed coconut oil, a heptyl, nonyl or undecyl radical, $R_2$ denotes a beta-hydroxyethyl group, and $R_3$ denotes a carboxymethyl group; and

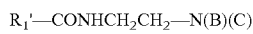

$R_1'$—CONHCH$_2$CH$_2$—N(B)(C)

in which:

B represents —CH$_2$CH$_2$OX',

C represents —(CH$_2$)$_z$—Y', with z=1 or 2,

X' denotes a —CH$_2$CH$_2$—COOH group, —CH$_2$—COOZ', —CH$_2$CH$_2$—COOH, —CH$_2$CH$_2$—COOZ' or a hydrogen atom, Y' denotes —COOH, —COOZ', —CH$_2$—CHOH—SO$_3$Z' or a —CH$_2$—CHOH—SO$_3$H radical, Z' represents an ion of an alkaline or alkaline earth metal such as sodium, an ammonium ion or an ion issued from an organic amine, and $R_1'$ denotes an alkyl radical of an acid $R_1'$—COOH present in coconut oil or in hydrolysed linseed oil, an alkyl radical, such as a $C_7$, $C_9$, $C_{11}$ or $C_{13}$ alkyl radical, a $C_{17}$ alkyl radical and its iso form, or an unsaturated $C_{17}$ radical.

It is preferable that the amphoteric surfactant be selected from ($C_8$-$C_{24}$)-alkyl amphomonoacetates, ($C_8$-$C_{24}$)alkyl amphodiacetates, ($C_8$-$C_{24}$)alkyl amphomonopropionates, and ($C_8$-$C_{24}$)alkyl amphodipropionates These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

Preferably, the amphoteric surfactant may be a betaine.

The betaine-type amphoteric surfactant is preferably selected from the group consisting of alkylbetaines, alkylamidoalkylbetaines, sulfobetaines, phosphobetaines, and alkylamidoalkylsulfobetaines, in particular, ($C_8$-$C_{24}$)alkylbetaines, ($C_8$-$C_{24}$)alkylamido($C_1$-$C_8$)alkylbetaines, sulphobetaines, and ($C_8$-$C_{24}$)alkylamido($C_1$-$C_8$)alkylsulphobetaines. In one embodiment, the amphoteric surfactants of betaine type are chosen from ($C_8$-$C_{24}$)alkylbetaines, ($C_8$-$C_{24}$)alkylamido($C_1$-$C_8$)alkylsulphobetaines, sulphobetaines, and phosphobetaines.

Non-limiting examples that may be mentioned include the compounds classified in the CTFA dictionary, 9th edition, 2002, under the names cocobetaine, laurylbetaine, cetylbetaine, coco/oleamidopropylbetaine, cocamidopropylbetaine, palmitamidopropylbetaine, stearamidopropylbetaine, cocamidoethylbetaine, cocamidopropylhydroxysultaine, oleamidopropylhydroxysultaine, cocohydroxysultaine, laurylhydroxysultaine, and cocosultaine, alone or as mixtures.

The betaine-type amphoteric surfactant is preferably an alkylbetaine and an alkylamidoalkylbetaine, in particular cocobetaine and cocamidopropylbetaine.

The amount of the (d) amphoteric surfactant is not limited, and may range from 0.1 to 25% by weight, preferably from 0.5 to 20% by weight, and more preferably from 1 to 15% by weight, relative to the total weight of the composition.

[Water]

The cosmetic composition according to the present invention comprises water.

The amount of water is not limited, and may be from 50 to 90% by weight, preferably from 55 to 80% by weight, and more preferably 60 to 75% by weight, relative to the total weight of the composition.

[Additional Surfactant]

The cosmetic composition according to the present invention may comprise at least one nonionic surfactant different from the above (b) and/or at least one anionic surfactant and/or at least one cationic surfactant. A single type of additional surfactant may be used, but two or more different types of additional surfactant may be used in combination.

As the additional surfactant, at least one nonionic surfactant with an HLB value less than 8.0 or more than 14.0 may be used.

As the additional nonionic surfactant, mention may be made of those listed for the above (b) except that the additional nonionic surfactant has an HLB value less than 8.0, preferably less than 9.0, and more preferably less than 10.0, and more than 14.0, preferably more than 13.5, and more preferably more than 13.0.

As the additional surfactant, at least one cationic surfactant and/or at least one anionic surfactant may be used.

(Cationic Surfactant)

The cationic surfactant is not limited. The cationic surfactant may be selected from the group consisting of optionally polyoxyalkylenated, primary, secondary or tertiary fatty amine salts, quaternary ammonium salts, and mixtures thereof.

Examples of quaternary ammonium salts that may be mentioned include, but are not limited to: those of general formula (I) below:

wherein $R_1$, $R_2$, $R_3$, and $R_4$, which may be identical or different, are chosen from linear and branched aliphatic radicals comprising from 1 to 30 carbon atoms and optionally comprising heteroatoms such as oxygen, nitrogen, sulfur and halogens. The aliphatic radicals may be chosen, for example, from alkyl, alkoxy, $C_2$-$C_6$ polyoxyalkylene, alkylamide, ($C_{12}$-$C_{22}$)alkylamido($C_2$-$C_6$)alkyl, ($C_{12}$-$C_{22}$)alkylacetate and hydroxyalkyl radicals; and aromatic radicals such as aryl and alkylaryl; and $X^-$ is chosen from halides, phosphates, acetates, lactates, ($C_2$-$C_6$) alkyl sulfates and alkyl- or alkylaryl-sulfonates; quaternary ammonium salts of imidazoline, for instance those of formula (II) below:

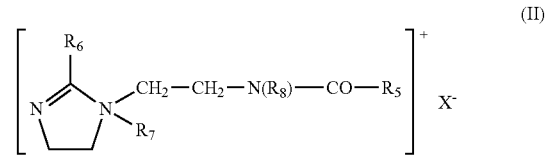

wherein:

$R_5$ is chosen from alkenyl and alkyl radicals comprising from 8 to 30 carbon atoms, for example fatty acid derivatives of tallow or of coconut;

$R_6$ is chosen from hydrogen, $C_1$-$C_4$ alkyl radicals, and alkenyl and alkyl radicals comprising from 8 to 30 carbon atoms;

$R_7$ is chosen from $C_1$-$C_4$ alkyl radicals;

$R_8$ is chosen from hydrogen and $C_1$-$C_4$ alkyl radicals; and $X^-$ is chosen from halides, phosphates, acetates, lactates, alkyl sulfates, alkyl sulfonates, and alkylaryl sulfonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Examples of such products include, but are not limited to, Quaternium-27 (CTFA 1997) and Quaternium-83 (CTFA 1997), which are sold under the names "Rewoquat®" W75, W90, W75PG and W75HPG by the company Witco;

diquaternary ammonium salts of formula (III):

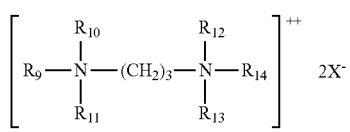

wherein:

$R_9$ is chosen from aliphatic radicals comprising from 16 to 30 carbon atoms;

$R_{10}$ is chosen from hydrogen or alkyl radicals comprising from 1 to 4 carbon atoms or a group $(R_{16a})(R_{17a})(R_{18a})N^+(CH_2)_3$;

$R_{11}$, $R_{12}$, $R_{13}$, $R_{14}$, $R_{16a}$, $R_{17a}$, and $R_{18a}$, which may be identical or different, are chosen from hydrogen and alkyl radicals comprising from 1 to 4 carbon atoms; and $X^-$ is chosen from halides, acetates, phosphates, nitrates, ethyl sulfates, and methyl sulfates.

An example of one such diquaternary ammonium salt is FINQUAT CT-P of FINETEX (Quaternium-89) or FINQUAT CT of FINETEX (Quaternium-75); and quaternary ammonium salts comprising at least one ester function, such as those of formula (IV) below:

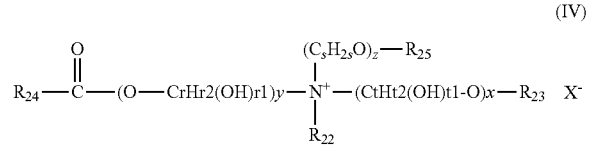

wherein:

$R_{22}$ is chosen from $C_1$-$C_6$ alkyl radicals and $C_1$-$C_6$ hydroxyalkyl and dihydroxyalkyl radicals;

$R_{23}$ is chosen from:

the radical blow:

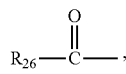

linear and branched, saturated and unsaturated $C_1$-$C_{22}$ hydrocarbon-based radicals $R_{27}$, and hydrogen, $R_{25}$ is chosen from:

the radical below:

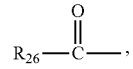

linear and branched, saturated and unsaturated $C_1$-$C_6$ hydrocarbon-based radicals $R_{29}$, and hydrogen, $R_{24}$, $R_{26}$, and $R_{28}$, which may be identical or different, are chosen from linear and branched, saturated and unsaturated, $C_7$-$C_{21}$, hydrocarbon-based radicals;

r, s, and t, which may be identical or different, are chosen from integers ranging from 2 to 6;

each of r1 and t1, which may be identical or different, is 0 or 1, and r2+r1=2r and t1+2t=2t;

y is chosen from integers ranging from 1 to 10;

x and z, which may be identical or different, are chosen from integers ranging from 0 to 10;

$X^-$ is chosen from simple and complex, organic and inorganic anions; with the proviso that the sum x+y+z ranges from 1 to 15, that when x is 0, $R_{23}$ denotes $R_{27}$, and that when z is 0, $R_{25}$ denotes $R_{29}$. $R_{22}$ may be chosen from linear and branched alkyl radicals. In one embodiment, $R_{22}$ is chosen from linear alkyl radicals. In another embodiment, $R_{22}$ is chosen from methyl, ethyl, hydroxyethyl, and dihydroxypropyl radicals, for example methyl and ethyl radicals. In one embodiment, the sum x+y+z ranges from 1 to 10. When $R_{23}$ is a hydrocarbon-based radical $R_{27}$, it may be long and comprise from 12 to 22 carbon atoms, or short and comprise from 1 to 3 carbon atoms. When $R_{25}$ is a hydrocarbon-based radical $R_{29}$, it may comprise, for example, from 1 to 3 carbon atoms. By way of a non-limiting example, in one embodiment, $R_{24}$, $R_{26}$, and $R_{28}$, which may be identical or different, are chosen from linear and branched, saturated and unsaturated, $C_{11}$-$C_{21}$ hydrocarbon-based radicals, for example from linear and branched, saturated and unsaturated $C_{11}$-$C_{21}$ alkyl and alkenyl radicals. In another embodiment, x and z, which may be identical or different, are 0 or 1. In one embodiment, y is equal to 1. In another embodiment, r, s and t, which may be identical or different, are equal to 2 or 3, for example equal to 2. The anion $X^-$ may be chosen from, for example, halides, such as chloride, bromide, and iodide; and $C_1$-$C_4$ alkyl sulfates, such as methyl sulfate. However, methanesulfonate, phosphate, nitrate, tosylate, an anion derived from an organic acid, such as acetate and lactate, and any other anion that is compatible with the ammonium comprising an ester function, are other non-limiting examples of anions that may be used according to the invention. In one embodiment, the anion $X^-$ is chosen from chloride and methyl sulfate.

In another embodiment, the ammonium salts of formula (IV) may be used, wherein:

$R_{22}$ is chosen from methyl and ethyl radicals, x and y are equal to 1;

z is equal to 0 or 1;

r, s and t are equal to 2;

$R_{23}$ is chosen from:

the radical below:

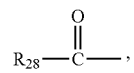

methyl, ethyl, and $C_{14}$-$C_{22}$ hydrocarbon-based radicals, hydrogen;

$R_{25}$ is chosen from:
the radical below:

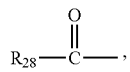

and hydrogen;
$R_{24}$, $R_{26}$, and $R_{28}$, which may be identical or different, are chosen from linear and branched, saturated and unsaturated, $C_{13}$-$C_{17}$ hydrocarbon-based radicals, for example from linear and branched, saturated and unsaturated, $C_{13}$-$C_{17}$ alkyl and alkenyl radicals.

In one embodiment, the hydrocarbon-based radicals are linear.

Non-limiting examples of compounds of formula (IV) that may be mentioned include salts, for example chloride and methyl sulfate, of diacyloxyethyl-dimethylammonium, of diacyloxyethyl-hydroxyethyl-methylammonium, of monoacyloxyethyl-dihydroxyethyl-methylammonium, of triacyloxyethyl-methylammonium, of monoacyloxyethyl-hydroxyethyl-dimethyl-ammonium, and mixtures thereof. In one embodiment, the acyl radicals may comprise from 14 to 18 carbon atoms, and may be derived, for example, from a plant oil, for instance palm oil and sunflower oil. When the compound comprises several acyl radicals, these radicals may be identical or different.

These products may be obtained, for example, by direct esterification of optionally oxyalkylenated triethanolamine, triisopropanolamine, alkyldiethanolamine or alkyldiisopropanolamine onto fatty acids or onto mixtures of fatty acids of plant or animal origin, or by transesterification of the methyl esters thereof. This esterification may be followed by a quaternization using an alkylating agent chosen from alkyl halides, for example methyl and ethyl halides; dialkyl sulfates, for example dimethyl and diethyl sulfates; methyl methanesulfonate; methyl para-toluenesulfonate; glycol chlorohydrin; and glycerol chlorohydrin.

Such compounds are sold, for example, under the names Dehyquart® by the company Cognis, Stepanquat® by the company Stepan, Noxamium® by the company Ceca, and "Rewoquat® WE 18" by the company Rewo-Goldschmidt.

Other non-limiting examples of ammonium salts that may be used in the compositions according to the invention include the ammonium salts comprising at least one ester function described in U.S. Pat. Nos. 4,874,554 and 4,137,180.

Among the quaternary ammonium salts mentioned above that may be used in compositions according to the invention include, but are not limited to, those corresponding to formula (I), for example tetraalkylammonium chlorides, for instance dialkyldimethylammonium and alkyltrimethylammonium chlorides in which the alkyl radical comprises from about 12 to 22 carbon atoms, such as behenyltrimethylammonium, distearyldimethylammonium, cetyltrimethylammonium and benzyldimethylstearylammonium chloride; palmitylamidopropyltrimethylammonium chloride; and stearamidopropyldimethyl(myristyl acetate)ammonium chloride, sold under the name "Ceraphyl® 70" by the company Van Dyk.

According to one embodiment, the cationic surfactant that may be used in the compositions of the invention is chosen from quaternary ammonium salts, for example from behenyltrimethylammonium chloride, cetyltrimethylammonium chloride, Quaternium-83, Quaternium-87, Quaternium-22, behenylamidopropyl-2,3-dihydroxypropyldimethylammo-nium chloride, palmitylamidopropyltrimethylammonium chloride, and stearamidopropyldimethylamine.

(Anionic Surfactant)

The anionic surfactant is not limited. The anionic surfactants may be chosen in particular from anionic derivatives of proteins of vegetable origin or of silk proteins, phosphates and alkyl phosphates, carboxylates, sulphosuccinates, amino acid derivatives, alkyl sulphates, alkyl ether sulphates, sulphonates, isethionates, taurates, alkyl sulphoacetates, polypeptides, anionic derivatives of alkyl polyglucosides, and their mixtures.

1) Anionic derivatives of proteins of vegetable origin are protein hydrolysates comprising a hydrophobic group, it being possible for the said hydrophobic group to be naturally present in the protein or to be added by reaction of the protein and/or of the protein hydrolysate with a hydrophobic compound. The proteins are of vegetable origin or derived from silk, and the hydrophobic group can in particular be a fatty chain, for example an alkyl chain comprising from 10 to 22 carbon atoms. Mention may more particularly be made, as anionic derivatives of proteins of vegetable origin, of apple, wheat, soybean or oat protein hydrolysates comprising an alkyl chain having from 10 to 22 carbon atoms, and their salts. The alkyl chain can in particular be a lauryl chain and the salt can be a sodium, potassium and/or ammonium salt.

Thus, mention may be made, as protein hydrolysates comprising a hydrophobic group, for example, of salts of protein hydrolysates where the protein is a silk protein modified by lauric acid, such as the product sold under the name Kawa Silk by Kawaken; salts of protein hydrolysates where the protein is a wheat protein modified by lauric acid, such as the potassium salt sold under the name Aminofoam W OR by Croda (CTFA name: potassium lauroyl wheat amino acids) and the sodium salt sold under the name Proteol LW 30 by Seppic (CTFA name: sodium lauroyl wheat amino acids); salts of protein hydrolysates where the protein is an oat protein comprising an alkyl chain having from 10 to 22 carbon atoms and more especially salts of protein hydrolysates where the protein is an oat protein modified by lauric acid, such as the sodium salt sold under the name Proteol OAT (30% aqueous solution) by Seppic (CTFA name: sodium lauroyl oat amino acids); or salts of apple protein hydrolysates comprising an alkyl chain having from 10 to 22 carbon atoms, such as the sodium salt sold under the name Proteol APL (30% aqueous/glycol solution) by Seppic (CTFA name: sodium cocoyl apple amino acids). Mention may also be made of the mixture of lauroyl amino acids (aspartic acid, glutamic acid, glycine, alanine) neutralized with sodium N-methylglycinate sold under the name Proteol SAV 50 S by Seppic (CTFA name: sodium cocoyl amino acids).

2) Mention may be made, as phosphates and alkyl phosphates, for example, of monoalkyl phosphates and dialkyl phosphates, such as lauryl monophosphate, sold under the name MAP 20® by Kao Chemicals, the potassium salt of dodecyl phosphate, the mixture of mono- and diesters (predominantly diester) sold under the name Crafol AP-31® by Cognis, the mixture of octyl phosphate monoester and diester, sold under the name Crafol AP-20® by Cognis, the mixture of ethoxylated (7 mol of EO) 2-butyloctyl phosphate monoester and diester, sold under the name Isofol 12 7 EO-Phosphate Ester® by Condea, the potassium or triethanolamine salt of mono($C_{12}$-$C_{13}$)alkyl phosphate, sold under the references Arlatone MAP 230K-40® and Arlatone MAP 230T-60® by Uniqema, potassium lauryl phosphate, sold under the name Dermalcare MAP XC-99/09® by Rhodia Chimie, and potassium cetyl phosphate, sold under the name Arlatone MAP 160K by Uniqema.

3) Mention may be made, as carboxylates, of:
   amido ether carboxylates (AEC), such as sodium lauryl amido ether carboxylate (3 EO), sold under the name Akypo Foam 30® by Kao Chemicals;
   polyoxyethylenated carboxylic acid salts, such as oxyethylenated (6 EO) sodium lauryl ether carboxylate (65/25/10 $C_{12}$-$C_{14}$-$C_{16}$), sold under the name Akypo Soft 45 NV® by Kao Chemicals, polyoxyethylenated and carboxymethylated fatty acids originating from olive oil, sold under the name Olivem 400® by Biologia E Tecnologia, or oxyethylenated (6 EO) sodium tridecyl ether carboxylate, sold under the name Nikkol ECTD-6NEX® by Nikkol; and
   salts of fatty acids (soaps) having a $C_6$ to $C_{22}$ alkyl chain which are neutralized with an organic or inorganic base, such as potassium hydroxide, sodium hydroxide, triethanolamine, N-methylglucamine, lysine and arginine.

4) Mention may in particular be made, as amino acid derivatives, of alkali salts of amino acids, such as:
   sarcosinates, such as sodium lauroyl sarcosinate, sold under the name Sarkosyl NL 97® by Ciba or sold under the name Oramix L 30® by Seppic, sodium myristoyl sarcosinate, sold under the name Nikkol Sarcosinate MN® by Nikkol, or sodium palmitoyl sarcosinate, sold under the name Nikkol Sarcosinate PN® by Nikkol;
   alaninates, such as sodium N-lauroyl-N-methylamidopropionate, sold under the name Sodium Nikkol Alaninate LN 30® by Nikkol or sold under the name Alanone ALE® by Kawaken, or triethanolamine N-lauroyl-N-methylalanine, sold under the name Alanone ALTA® by Kawaken;
   glutamates, such as triethanolamine monococoyl glutamate, sold under the name Acylglutamate CT-12® by Ajinomoto, triethanolamine lauroyl glutamate, sold under the name Acylglutamate LT-12® by Ajinomoto;
   aspartates, such as the mixture of triethanolamine N-lauroyl aspartate and triethanolamine N-myristoyl aspartate, sold under the name Asparack® by Mitsubishi;
   glycine derivatives (glycinates), such as sodium N-cocoyl glycinate, sold under the names Amilite GCS-12® and Amilite GCK 12 by Ajinomoto;
   citrates, such as the citric monoester of oxyethylenated (9 mol) coco alcohols, sold under the name Witconol EC 1129 by Goldschmidt, and
   galacturonates, such as sodium dodecyl D-galactoside uronate, sold by Soliance.

5) Mention may be made, as sulphosuccinates, for example, of oxyethylenated (3 EO) lauryl (70/30 $C_{12}$/$C_{14}$) alcohol monosulphosuccinate, sold under the names Setacin 103 Special® and Rewopol SB-FA 30 K 4® by Witco, the disodium salt of a hemisulphosuccinate of $C_{12}$-$C_{14}$ alcohols, sold under the name Setacin F Special Paste® by Zschimmer Schwarz, oxyethylenated (2 EO) disodium oleamidosulphosuccinate, sold under the name Standapol SH 135® by Cognis, oxyethylenated (5 EO) lauramide monosulphosuccinate, sold under the name Lebon A-5000® by Sanyo, the disodium salt of oxyethylenated (10 EO) lauryl citrate monosulphosuccinate, sold under the name Rewopol SB CS 50® by Witco, or ricinoleic monoethanolamide monosulphosuccinate, sold under the name Rewoderm S 1333® by Witco. Use may also be made of polydimethylsiloxane sulphosuccinates, such as disodium PEG-12 dimethicone sulphosuccinate, sold under the name Mackanate-DC 30 by MacIntyre.

6) Mention may be made, as alkyl sulphates, for example, of triethanolamine lauryl sulphate (CTFA name: TEA lauryl sulphate), such as the product sold by Huntsman under the name Empicol TL40 FL or the product sold by Cognis under the name Texapon T42, which products are at 40% in aqueous solution. Mention may also be made of ammonium lauryl sulphate (CTFA name: ammonium lauryl sulphate), such as the product sold by Huntsman under the name Empicol AL 30FL, which is at 30% in aqueous solution.

7) Mention may be made, as alkyl ether sulphates, for example, of sodium lauryl ether sulphate (CTFA name: sodium laureth sulphate), such as that sold under the names Texapon N40 and Texapon AOS 225 UP by Cognis, or ammonium lauryl ether sulphate (CTFA name: ammonium laureth sulphate), such as that sold under the name Standapol EA-2 by Cognis.

8) Mention may be made, as sulphonates, for example, of α-olefinsulphonates, such as sodium α-olefinsulphonate ($C_{14}$-$C_{16}$), sold under the name Bio-Terge AS-40® by Stepan, sold under the names Witconate AOS Protégé® and Sulframine AOS PH 12® by Witco or sold under the name Bio-Terge AS-40 CG® by Stepan, secondary sodium olefinsulphonate, sold under the name Hostapur SAS 30® by Clariant; or linear alkylarylsulphonates, such as sodium xylenesulphonate, sold under the names Manrosol SXS30®, Manrosol SXS40® and Manrosol SXS93® by Manro.

9) Mention may be made, as isethionates, of acylisethionates, such as sodium cocoylisethionate, such as the product sold under the name Jordapon CI P® by Jordan.

10) Mention may be made, as taurates, of the sodium salt of palm kernel oil methyltaurate, sold under the name Hostapon CT Paté® by Clariant; N-acyl-N-methyltaurates, such as sodium N-cocoyl-N-methyltaurate, sold under the name Hostapon LT-SF® by Clariant or sold under the name Nikkol CMT-30-T® by Nikkol, or sodium palmitoyl methyltaurate, sold under the name Nikkol PMT® by Nikkol.

11) The anionic derivatives of alkyl polyglucosides can in particular be citrates, tartrates, sulphosuccinates, carbonates and glycerol ethers obtained from alkyl polyglucosides. Mention may be made, for example, of the sodium salt of cocoylpolyglucoside (1,4) tartaric ester, sold under the name Eucarol AGE-ET® by Cesalpinia, the disodium salt of cocoylpolyglucoside (1,4) sulphosuccinic ester, sold under the name Essai 512 MP® by Seppic, or the sodium salt of cocoylpolyglucoside (1,4) citric ester, sold under the name Eucarol AGE-EC® by Cesalpinia.

It is preferable that the amino acid derivatives be acyl glycine derivatives or glycine derivatives, in particular acyl glycine salt.

The acyl glycine derivatives or glycine derivatives can be chosen from acyl glycine salts (or acyl glycinates) or glycine salts (or glycinates), and in particular from the following.

i) Acyl glycinates of formula (I):

R—HNCH$_2$COOX    (I)

in which
   R represents an acyl group R'C=O, with R', which represents a saturated or unsaturated, linear or branched, hydrocarbon chain, preferably comprising from 10 to 30 carbon atoms, preferably from 12 to 22 carbon atoms, preferably from 14 to 22 carbon atoms and better still from 16 to 20 carbon atoms, and
   X represents a cation chosen, for example, from the ions of alkali metals, such as Na, Li or K, preferably Na or K, the ions of alkaline earth metals, such as Mg, ammonium groups and their mixtures.

The acyl group can in particular be chosen from the lauroyl, myristoyl, behenoyl, palmitoyl, stearoyl, isostearoyl, olivoyl, cocoyl or oleoyl groups and their mixtures.

Preferably, R is a cocoyl group.

ii) Glycinates of following formula (II):

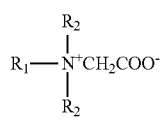
(II)

in which:
R$_1$ represents a saturated or unsaturated, linear or branched, hydrocarbon chain comprising from 10 to 30 carbon atoms, preferably from 12 to 22 carbon atoms and better still from 16 to 20 carbon atoms; R$_1$ is advantageously chosen from the lauryl, myristyl, palmityl, stearyl, cetyl, cetearyl or oleyl groups and their mixtures and preferably from the stearyl and oleyl groups, the R$_2$ groups, which are identical or different, represent an R"OH group, R" being an alkyl group comprising from 2 to 10 carbon atoms, preferably from 2 to 5 carbon atoms.

Mention may be made, as compound of formula (I), for example, of the compounds carrying the INCI name sodium cocoyl glycinate, such as, for example, Amilite GCS-12, sold by Ajinomoto, or potassium cocoyl glycinate, such as, for example, Amilite GCK-12 from Ajinomoto.

Use may be made, as compounds of formula (II), of dihydroxyethyl oleyl glycinate or dihydroxyethyl stearyl glycinate.

The amount of the additional surfactant(s) may be 0.01 wt % to 20 wt %, preferably 0.10 wt % to 10 wt %, and more preferably 1 wt % to 5 wt %, relative to the total weight of the composition.

[Polyol]

The cosmetic composition according to the present invention may comprise at least one polyol. A single type of polyol may be used, but two or more different types of polyol may be used in combination.

The term "polyol" here means an alcohol having two or more hydroxy groups, and does not encompass a saccharide or a derivative thereof. The derivative of a saccharide includes a sugar alcohol which is obtained by reducing one or more carbonyl groups of a saccharide, as well as a saccharide or a sugar alcohol in which the hydrogen atom or atoms in one or more hydroxy groups thereof has or have been replaced with at least one substituent such as an alkyl group, a hydroxyalkyl group, an alkoxy group, an acylgroup or a carbonyl group.

The polyol may be a $C_2$-$C_{12}$ polyol, preferably a $C_{2-9}$ polyol, comprising at least 2 hydroxy groups, and preferably 2 to 5 hydroxy groups.

The polyol may be a natural or synthetic polyol. The polyol may have a linear, branched or cyclic molecular structure.

The polyol may be selected from glycerins and derivatives thereof, and glycols and derivatives thereof. The polyol may be selected from the group consisting of glycerin, diglycerin, polyglycerin, ethyleneglycol, diethyleneglycol, propyleneglycol, dipropyleneglycol, butyleneglycol, pentyleneglycol, hexyleneglycol, 1,3-propanediol, and 1,5-pentanediol.

The polyol may be an alkylene oxide derivative represented by the following formula (I):

$$Z\text{---}\{O(AO)_l(EO)_m\text{---}(BO)_nH\}_a \quad (I)$$

wherein

Z denotes a residue obtained by removing hydroxyl group(s) from a compound having 3 to 9 hydroxyl groups;

AO denotes an oxyalkylene group having 3 to 4 carbon atoms;

EO denotes an oxyethylene group;

BO denotes an oxyalkylene group having 4 carbon atoms;

a denotes 3 to 9;

l, m, and n denote the average addition mole numbers of AO, EU and BO, respectively, and 1≤l≤50, 1≤m≤50 and 0.5≤n≤5;

a weight ratio of AO to EO (AO/EO) ranges from 1/5 to 5/1; and

AO and EO may have been added randomly or in the form of blocks.

The aforementioned alkylene oxide derivatives may be a single type thereof, or a mixture of plural types thereof.

In the alkylene oxide derivative represented by formula (I), Z denotes a residue obtained by removing hydroxyl groups from a compound having 3 to 9 hydroxyl groups, and a denotes the number of hydroxyl groups of the compound and is 3 to 9. As examples of compounds having 3 to 9 hydroxyl groups, mention may be made of, for example, in the case of a=3, glycerin, and trimethylolpropane; in the case of a=4, erythritol, pentaerythritol, sorbitol, alkylglycosides, and diglycerin; in the case of a=5, xylitol; in the case of a=6, dipentaerythritol, sorbitol, and inositol; in the case of a=8, sucrose, and trehalose; in the case of a=9, maltitol; mixtures thereof; and the like. Preferably, Z denotes a residue obtained by removing hydroxyl group(s) from a compound having 3 to 6 hydroxyl groups, and a satisfies 3≤a≤6. As the compound having 3 to 9 hydroxyl groups, glycerin or trimethylolpropane is preferable, and in particular, glycerin is preferable. In the case of a≤2, poor compatibility with oil components such as fats and oils is exhibited, and blending stability in an oil-based formulation tends to be impaired. In the case of 10≤a, stickiness occurs.

AO denotes an oxyalkylene group having 3 to 4 carbon atoms. As examples thereof, mention may be made of, for example, an oxypropylene group, an oxybutylene group (an oxy-n-butylene group, an oxyisobutylene group, or an oxy-t-butylene group), an oxytrimethylene group, an oxytetramethylene group, and the like. The oxypropylene group and oxybutylene group are preferable, and the oxypropylene group is more preferable.

l denotes the average addition mole number of AO, and satisfies 1≤l≤50, and preferably 2≤l≤20.

m denotes the average addition mole number of EO, and satisfies 1≤m≤50, and preferably 2≤m≤20. If l is 0, stickiness occurs. On the other hand, if l exceeds 50, moisturizing effects are decreased. In addition, if m is 0, moisturizing effects are decreased. On the other hand, if m exceeds 50, stickiness occurs.

The weight ratio of AO to EO (AO/EO) ranges from 1/5 to 5/1, and preferably ranges from 1/4 to 4/1. If AO/EO is below 1/5, stickiness occurs. On the other hand, if AO/EO exceeds 5/1, the moisturizing sensation is decreased. The order of adding AO and EO is not particularly specified. AO and EO can be added randomly or in the form of blocks. In order to obtain superior effects of preventing skin roughness, AO and EO are preferably added randomly.

BO denotes an oxyalkylene group having 4 carbon atoms. As examples thereof, mention may be made of, for example, an oxybutylene group (an oxy-n-butylene group, an oxy-isobutylene group, or an oxy-t-butylene group), an oxytetramethylene group, and the like. The oxybutylene group is preferable.

n denotes the average addition mole number of BO, and satisfies $0.5 < n \le 5$, preferably $0.8 \le n \le 3$, and more preferably $1 \le n \le 3$. If n is below 0.5, stickiness occurs. On the other hand, if n exceeds 5, moisturizing effects are decreased. In formula (I), it is necessary that $(BOA)_n$ bonds to the terminal hydrogen atom.

The alkylene oxide derivatives represented by formula (I) can be produced by means of known methods. For example, the alkylene oxide derivatives represented by formula (I) can be obtained by additive-polymerizing ethylene oxide and an alkylene oxide having 3 to 4 carbon atoms to a compound having 3 to 9 hydroxyl groups, and subsequently reacting with an alkylene oxide having 4 carbon atoms.

When additive-polymerizing ethylene oxide and an alkylene oxide having 3 to 4 carbon atoms to a compound having 3 to 9 hydroxyl groups, the ethylene oxide and alkylene oxide may be polymerized randomly or in the form of blocks.

Among the alkylene oxide derivatives represented by formula (I), preferable examples of the aforementioned alkylene oxide derivatives include, for example, an alkylene oxide derivative (polyoxybutylene polyoxyethylene polyoxypropylene glycerol) represented by formula (II) shown below:

$$\text{Gly-}[O(PO)_s(EO)_t\text{—}(BO)_uH]_3 \quad\quad (II)$$

wherein

Gly denotes a residue obtained by removing hydroxyl groups from glycerin;

PO denotes an oxypropylene group;

EO denotes an oxyethylene group;

s and t denote the average addition mole numbers of PO and EO, respectively, and have a value ranging from 1 to 50;

the weight ratio of PO to EO (PO/EO) ranges from 1/5 to 5/1;

BO denotes an oxyalkylene group having 4 carbon atoms; and u denotes the average addition mole number of BO, and ranges from 0.5 to 5.

The aforementioned alkylene oxide derivative represented by formula (II) can be obtained by adding propylene oxide and ethylene oxide to glycerin, in the ratio of 3 to 150 mole equivalents of each of propylene oxide and ethylene oxide with respect to glycerin, and subsequently, adding the alkylene oxide having 4 carbon atoms in the ratio of 1.5 to 15 mole equivalents thereof with respect to glycerin.

In the case of adding the aforementioned alkylene oxides to glycerin, the addition reactions are carried out with an alkali catalyst, a phase transfer catalyst, a Lewis acid catalyst, or the like. In general, an alkali catalyst such as potassium hydroxide is preferably employed.

Among the alkylene oxide derivatives represented by formula (I), more preferable derivatives are obtained by adding 6 to 10 mol of ethylene oxide and 3 to 7 mol of propylene oxide to glycerin, and subsequently, adding 2 to 4 mol of butylene oxide.

Among the alkylene oxide derivatives represented by formula (I), a further more preferable derivative is polyoxybutylene polyoxyethylene polyoxypropylene glycerol, which is obtained by adding 8 mol of ethylene oxide and 5 mol of propylene oxide to glycerin, and subsequently, adding 3 mol of butylene oxide, and which has an INCI name of PEG/PPG/polybutylene glycol-8/5/3 glycerin. PEG/PPG/polybutylene glycol-8/5/3 glycerin is commercially available under the trade name of WILBRIDE S-753 from NOF Corporation.

The polyol may be present in an amount ranging from 0.01% to 30% by weight, and preferably from 0.1% to 20% by weight, such as from 1% to 10% by weight, relative to the total weight of the composition.

[Thickening Agent]

The cosmetic composition according to the present invention may comprise at least one thickening agent. A single type of thickening agent may be used, but two or more different types of thickening agent may be used in combination.

The thickening agent may be selected from organic and inorganic thickeners.

The organic thickeners may be chosen at least one of:
  (i) associative thickeners;
  (ii) crosslinked acrylic acid homopolymers;
  (iii) crosslinked copolymers of (meth)acrylic acid and of $(C_1\text{-}C_6)$alkyl acrylate;
  (iv) nonionic homopolymers and copolymers comprising at least one of ethylenically unsaturated ester monomers and ethylenically unsaturated amide monomers;
  (v) ammonium acrylate homopolymers and copolymers of ammonium acrylate and of acrylamide;
  (vi) polysaccharides; and
  (vii) $C_{12}\text{-}C_{30}$ fatty alcohols.

The thickening agent is preferably selected from associative thickeners.

As used herein, the expression "associative thickener" means an amphiphilic thickener comprising both hydrophilic units and hydrophobic units, for example, comprising at least one $C_8\text{-}C_{30}$ fatty chain and at least one hydrophilic unit.

Associative thickeners disclosed herein that may be used are associative polymers chosen from:
  (a) nonionic amphiphilic polymers comprising at least one fatty chain and at least one hydrophilic unit;
  (b) anionic amphiphilic polymers comprising at least one hydrophilic unit and at least one fatty-chain unit;
  (c) cationic amphiphilic polymers comprising at least one hydrophilic unit and at least one fatty-chain unit; and
  (d) amphoteric amphiphilic polymers comprising at least one hydrophilic unit and at least one fatty-chain unit;
wherein the fatty chain unit contains from 10 to 30 carbon atoms.

The nonionic amphiphilic polymers comprising at least one fatty chain and at least one hydrophilic unit may be chosen from one or more of:

(1) celluloses modified with groups comprising at least one fatty chain; examples that may be mentioned include:
  hydroxyethylcelluloses modified with at least one group comprising at least one fatty chain, for example, the at least one group may be chosen from alkyl, arylalkyl, and alkylaryl groups, and in which the alkyl groups may be $C_8\text{-}C_{22}$, such as the product NATROSOL® Plus Grade 330 CS, comprising $C_{16}$ alkyls, sold by the company Aqualon, or the product BERMOCOLL® EHM 100 sold by the company Berol Nobel,
  celluloses modified with at least one polyalkylene glycol alkylphenyl ether group, such as the product AMERCELL® Polymer HM-1500, comprising polyethylene glycol (15) nonylphenyl ether, sold by the company Amerchol.

(2) hydroxypropyl guars modified with at least one group comprising at least one fatty chain, such as the product ESAFLOR® HM 22, comprising $C_{22}$ alkyl chains, sold by the company Lamberti, and the products MIRACARE®

XC95-3, comprising $C_{14}$ alkyl chains, and RE205-1, comprising $C_{20}$ alkyl chains, sold by the company Rhodia Chimie.

(3) polyether urethanes comprising at least one fatty chain, such as $C_{10}$-$C_{30}$ alkyl and alkenyl groups, for instance the products DAPRAL® T 210 and DAPRAL® T 212 sold by the company Akzo and the products ACULYN® 44 and ACULYN® 46 sold by the company Rohm & Haas.

(4) copolymers of vinylpyrrolidone and of hydrophobic fatty-chain monomers; examples that may be mentioned include:

the products ANTARON® V216 and GANEX® V216, comprising vinylpyrrolidone/hexadecene copolymers, sold by the company I.S.P.;

the products ANTARON® V220 and GANEX® V220, comprising vinylpyrrolidone/eicosene copolymers, sold by the company I.S.P.;

(5) copolymers of $C_1$-$C_6$ alkyl acrylates and methacrylates and of amphiphilic monomers comprising at least one fatty chain, such as, for example, the oxyethylenated methyl methacrylate/stearyl acrylate copolymer sold by the company Goldschmidt under the name ANTIL® 208; and (6) copolymers of hydrophilic acrylates and methacrylates and of hydrophobic monomers comprising at least one fatty chain, such as, for example, the polyethylene glycol methacrylate/lauryl methacrylate copolymer.

Among the anionic amphiphilic polymers disclosed herein comprising at least one hydrophilic unit and at least one fatty-chain unit, mention may be made of those comprising at least one fatty-chain allyl ether unit and at least one hydrophilic unit comprising an ethylenic unsaturated anionic monomer, such as those comprising at least one of vinylcarboxylic acid, acrylic acid, and methacrylic acid, wherein the fatty-chain allyl ether unit corresponds to the monomer of formula (V) below:

$$CH_2=C(R_5)CH_2OB_qR \qquad (V)$$

in which $R_5$ is chosen from hydrogen atoms and methyl groups;

B denotes an ethyleneoxy radical;

q is chosen from integers ranging from 0 to 100; and

R denotes a hydrocarbon-based radical chosen from alkyl, arylalkyl, aryl, alkylaryl, and cycloalkyl radicals, containing from 10 to 30 carbon atoms, such as 10 to 24 carbon atoms and further such as 12 to 18 carbon atoms.

A unit of formula (V) that may be used according to certain embodiments is a unit in which R5 denotes H, q is equal to 10, and R denotes a stearyl, i.e., $C_{18}$, radical.

Anionic amphiphilic polymers of this type are described and prepared, for example, according to an emulsion polymerization process in European Patent No. EP-0 216 479 B2.

Among these anionic amphiphilic polymers that may be used according to one embodiment are polymers formed from 20% to 60% by weight of acrylic acid and/or of methacrylic acid, from 5% to 60% by weight of lower alkyl(meth)acrylates, from 2% to 50% by weight of the at least one fatty-chain allyl ether of formula (V), and from 0% to 1% by weight of a crosslinking agent which comprise one or more well-known copolymerizable unsaturated polyethylenic monomers, for instance diallyl phthalate, allyl(meth) acrylate, divinylbenzene, (poly)ethylene glycol dimethacrylate, and methylenebisacrylamide.

Among the latter polymers, those that may be used include crosslinked terpolymers of methacrylic acid, of ethyl acrylate and of polyethylene glycol (10 EO) stearyl ether (Steareth-10), such as those sold by the company Ciba under the names SALCARE® SC 80 and SALCARE® SC 90, which are aqueous 30% emulsions of a crosslinked terpolymer of 40% methacrylic acid, of 50% ethyl acrylate, and of 10% steareth-10 allyl ether.

The anionic amphiphilic polymers can also be chosen from those comprising at least one unsaturated olefinic carboxylic acid hydrophilic unit, and at least one hydrophobic unit of the type such as a ($C_{10}$-$C_{30}$) alkyl ester of an unsaturated carboxylic acid, which, according to one embodiment, may be chosen from those in which the unsaturated olefinic carboxylic acid hydrophilic unit corresponds to the monomer of formula (VI) below:

(VI)

in which $R_6$ is chosen from hydrogen atoms, methyl groups, and ethyl groups, such as acrylic acid, methacrylic acid, and ethacrylic acid units, and in which the hydrophobic unit of the type such as a ($C_{10}$-$C_{30}$) alkyl ester of an unsaturated carboxylic acid corresponds to the monomer of formula (VII) below:

$$H_2C=CR_6-CO-OR_7 \qquad (VII)$$

in which formula $R_6$ is chosen from hydrogen atoms, methyl groups, and ethyl groups, such as acrylate, methacrylate, and ethacrylate units, and such as hydrogen atoms, i.e., acrylate units, and methyl groups, i.e., methacrylate units; and $R_7$ is a $C_{10}$-$C_{30}$, such as $C_{12}$-$C_{22}$, alkyl radical.

($C_{10}$-$C_{30}$)Alkyl esters of unsaturated carboxylic acids disclosed herein comprise, for example, at least one of lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate, and dodecyl methacrylate.

Anionic amphiphilic polymers of this type are disclosed and prepared, for example, according to U.S. Pat. Nos. 3,915,921 and 4,509,949.

The anionic amphiphilic polymers that may be used in the composition disclosed herein may for example comprise polymers formed from a mixture of monomers. The anionic amphiphilic polymers may comprise at least one of the following monomers:

(i) acrylic acid, an ester of formula (VIII) below:

$$H_2C=CR_8-CO-OR_9 \qquad (VIII)$$

in which $R_8$ is chosen from hydrogen atoms and methyl groups, $R_9$ is an alkyl radical containing from 12 to 22 carbon atoms, and a crosslinking agent, such as, for example, those comprising from 95% to 60% by weight of acrylic acid, i.e., a hydrophilic unit, 4% to 40% by weight of $C_{10}$-$C_{30}$ alkyl acrylate, i.e., a hydrophobic unit, and 0% to 6% by weight of crosslinking polymerizable monomer, or 98% to 96% by weight of acrylic acid, i.e., a hydrophilic unit, 1% to 4% by weight of $C_{10}$-$C_{30}$ alkyl acrylate, i.e., a hydrophobic unit, and 0.1% to 0.6% by weight of crosslinking polymerizable monomer; and (ii) acrylic acid and lauryl methacrylate, such as the product formed from 66% by weight of acrylic acid and 34% by weight of lauryl methacrylate.

The said crosslinking agent is a monomer containing a group

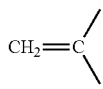

with at least one other polymerizable group whose unsaturated bonds are not conjugated. Mention may be made for example of polyallyl ethers such as polyallylsucrose and polyallylpentaerythritol.

Among the said polymers above, ones that may be used according to one embodiment are the products sold by the company Goodrich under the trade names PEMULEN® TR1, PEMULEN® TR2, CARBOPOL® 1382, such as, for example, PEMULEN® TR1, and the product sold by the company S.E.P.C. under the name COATEX® SX.

As anionic amphiphilic fatty-chain polymers, mention may also be made of the ethoxylated copolymer of methacrylic acid/methyl acrylate/alkyl dimethyl-meta-isopropenylbenzylisocyanate sold under the name VISCOPHOBE® DB 1000 by the company Amerchol.

The cationic amphiphilic polymers disclosed herein may be chosen from at least one of quaternized cellulose derivatives and polyacrylates containing amino side groups.

The quaternized cellulose derivatives comprise, for example, quaternized celluloses modified with at least one group comprising at least one fatty chain, such as alkyl, arylalkyl, and alkylaryl groups containing at least 8 carbon atoms, and quaternized hydroxyethylcelluloses modified with at least one group comprising at least one fatty chain, such as alkyl, arylalkyl, and alkylaryl groups containing at least 8 carbon atoms.

Quaternized or non-quaternized polyacrylates containing amino side groups, have, for example, hydrophobic groups, such as STEARETH® 20, comprising polyoxyethylenated (20) stearyl alcohol, and $(C_{10}\text{-}C_{30})$alkyl PEG-20 itaconate.

The alkyl radicals borne by the above quaternized celluloses or hydroxyethylcelluloses may contain from 8 to 30 carbon atoms.

The aryl radicals may be chosen from phenyl, benzyl, naphthyl, and anthryl groups.

Quaternized alkylhydroxyethylcelluloses containing $C_{8\text{-}C_{30}}$ fatty chains may be chosen from one or more of the products QUATRISOFT® LM 200, QUATRISOFT® LM-X 529-18-A, QUATRISOFT® LM-X 529-18B, comprising C12 alkyls, and QUATRISOFT® LM-X 529-8, comprising $C_{18}$ alkyls, sold by the company Amerchol, and the products CRODACEL® QM, CRODACEL® QL, comprising $C_{12}$ alkyls, and CRODACEL® QS, comprising $C_{18}$ alkyls, sold by the company Croda.

Polyacrylates comprising amino side chains may be chosen from at least one Starch.

Amphoteric amphiphilic polymers comprising at least one fatty chain, may be chosen from one or more of copolymers of methacrylamidopropyltrimethylammonium chloride/acrylic acid/$C_{10}$-$C_{30}$ alkyl methacrylate, the alkyl radical for example being a stearyl radical.

In certain embodiments, the associative thickeners in the cosmetic compositions disclosed herein have, in solution or in dispersion at a concentration of 1% active material in water, a viscosity, measured using a Rheomat RM 180 rheometer at 25° C., of greater than 0.1 ps, or for example of greater than 0.2 cp, at a shear rate of 200 $s^{-1}$.

(i) Among the crosslinked acrylic acid homopolymers that may be mentioned are those crosslinked with an allylic alcohol ether of the sugar series, such as, for example, the products sold under the names CARBOPOL® 980, 981, 954, 2984, and 5984 by the company Goodrich or the products sold under the names SYNTHALEN® M and SYNTHALEN® K by the company 3 VSA.

(ii) Among the crosslinked copolymers of (meth)acrylic acid and of $C_1$-$C_6$ alkyl acrylate that may be mentioned is the product sold under the name VISCOATEX® 538C by the company Coatex, which is a crosslinked copolymer of methacrylic acid and of ethyl acrylate as an aqueous dispersion containing 38% active material, and the product sold under the name ACULYN® 33 by the company Rohm & Haas, which is a crosslinked copolymer of acrylic acid and of ethyl acrylate as an aqueous dispersion containing 28% active material.

(iii) Among the nonionic homopolymers or copolymers comprising at least one of ethylenically unsaturated ester monomers and ethylenically unsaturated amide monomers, mention may be made of the products sold under the names: CYANAMER® P250 by the company Cytec, comprising polyacrylamide; PMMA MBX-8C by the company U.S. Cosmetics, comprising methyl methacrylate/ethylene glycol dimethacrylate copolymers; ACRYLOID® B66 by the company Rohm & Haas, comprising butyl methacrylate/methyl methacrylate copolymers; and BPA 500 by the company Kobo, comprising polymethyl methacrylate.

(iv) Among the ammonium acrylate homopolymers that may be mentioned is the product sold under the name MICROSAP® PAS 5193 by the company Hoechst. Copolymers of ammonium acrylate and of acrylamide may be, for example, chosen from one or more of the product sold under the name Bozepol C Nouveau or the product PAS 5193 sold by the company Hoechst, which are described and prepared for example in documents French Patent FR 2 416 723, and U.S. Pat. Nos. 2,798,053 and 2,923,692.

(v) The thickening polysaccharides may be chosen from at least one of glucans; modified or unmodified starches, such as those derived, for example, from cereals, for instance wheat, corn, and rice, from vegetables, for instance yellow pea, and tubers, for instance potato and cassava; amylose; amylopectin; glycogen; dextrans; celluloses and derivatives thereof, such as methylcelluloses, hydroxyalkylcelluloses, ethylhydroxyethylcelluloses, and carboxymethylcelluloses; mannans; xylans; lignins; arabans; galactans; galacturonans; chitin; chitosans; glucuronoxylans; arabinoxylans; xyloglucans; glucomannan; pectic acids, pectins; alginic acid; alginates; arabinogalactans; carrageenans; agars; glycosaminoglucans; gum arabics; gum tragacanths; ghatti gums; karaya gums; carob gums; and galactomannans, such as guar gums and nonionic derivatives thereof, for instant hydroxypropyl guar and xanthan gums.

In general, the compounds of this type that may be used according to certain embodiments disclosed herein are chosen from those described for example in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328, 1980, and in "Industrial Gums-Polysaccharides and their Derivatives", edited by Roy L. Whistler, Second Edition, published by Academic Press Inc. The content of these three publications is incorporated by reference herein.

Starches, guar gums, celluloses, and derivatives thereof may, for example, be used.

The guar gums may be modified or unmodified.

Unmodified guar gums may be, for example, chosen from at least one of the products sold under the name VID- OGUM® GH 175 by the company Unipectine and under the names MEYPRO®-GUAR 50 and JAGUAR® C by the company Meyhall.

The modified nonionic guar gums may be modified with $C_1$-$C_6$ hydroxyalkyl groups.

Hydroxyalkyl groups may be, for example, chosen from one or more of hydroxymethyl, hydroxyethyl, hydroxypropyl, and hydroxybutyl groups. These guar gums are known in the prior art and can be prepared, for example, by reacting the corresponding alkene oxides such as, for example, propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, may range from 0.4 to 1.2.

Such nonionic guar gums optionally modified with hydroxyalkyl groups are sold, for example, under the trade names JAGUAR® HP8, JAGUAR® HP60, JAGUAR® HP120, JAGUAR® DC 293, and JAGUAR HP 105 by the company RhodiaCelluloses may be, for example, chosen from at least one of hydroxyethylcelluloses and hydroxypropylcelluloses. Mention may be made of the products sold under the names KLUCEL® EF, KLUCEL® H, KLUCEL® LHF, KLUCEL® MF, and KLUCEL® G by the company Aqualon.

The fatty alcohols may be chosen from one or more of myristyl alcohol, cetyl alcohol, stearyl alcohol, and behenyl alcohol.

Mineral thickeners may be chosen from one or more clays.

The viscosity of the cosmetic composition according to the present invention is not particularly limited. The viscosity can be measured at 25° C. with viscosimeters or rheometers preferably with coneplan geometry. Preferably, the viscosity of the cosmetic composition according to the present invention can range, for example, from 1 to 2000 Pa·s, and preferably from 1 to 1000 Pa·s at 25° C. and 1 $s^{-1}$.

The thickening agent may be present in an amount ranging from 0.001% to 10% by weight, and preferably from 0.01% to 10% by weight, such as from 0.1% to 5% by weight, relative to the total weight of the composition.

[Other Ingredients]

The cosmetic composition according to the present invention may also comprise an effective amount of other ingredients, known previously elsewhere in lightening or coloring compositions, such as various common adjuvants, sequestering agents such as EDTA and etidronic acid, IN screening agents, silicones other than those mentioned before (such as with amine groups), preserving agents, vitamins or provitamins, for instance, panthenol, opacifiers, fragrances, plant extracts, cationic polymers and so on.

The cosmetic composition according to the present invention may further comprise at least one organic solvent. So the organic solvent is preferably water miscible. As the organic solvent, there may be mentioned, for example, $C_1$-$C_4$ alkanols, such as ethanol and isopropanol; aromatic alcohols such as benzyl alcohol and phenoxyethanol; analogous products; and mixtures thereof.

The organic water-soluble solvents may be present in an amount ranging from less than 10% by weight, preferably from 5% by weight or less, and more preferably from 1% by weight or less, relative to the total weight of the composition.

[Preparation and Properties]

The cosmetic composition according to the present invention can be prepared by mixing the above essential and optional ingredients in accordance with a conventional process. The conventional process includes mixing with a high pressure homogenizer (a high energy process). Alternatively, the cosmetic composition can be prepared by a low energy processes such as phase inversion temperature process (PIT), phase inversion concentration (PIC), autoemulsification, and the like.

The weight ratio of the (b) polyglyceryl fatty acid ester to the (a) oil may be from 0.3 to 6, preferably from 0.4 to 3, and more preferably from 0.5 to 1.5. In particular, the weight ratio of the (b) polyglyceryl fatty acid ester/the (a) oil is preferably 1 or less, such as from 0.3 to 1, preferably from 0.4 to 1, and more preferably from 0.5 to 1.

The cosmetic composition according to the present invention is in the form of a nano- or micro-emulsion.

The "micro-emulsion" may be defined in two ways, namely, in a broader sense and in a narrower sense. That is to say, there are one case ("microemulsion in the narrow sense") in which the microemulsion refers to a thermodynamically stable isotropic single liquid phase containing a ternary system having three ingredients of an oily component, an aqueous component and a surfactant, and the other case ("micro-emulsion in the broad sense") in which among thermodynamically unstable typical emulsion systems the microemulsion additionally includes those such emulsions presenting transparent or translucent appearances due to their smaller particle sizes (Satoshi Tomomasa, et al., OilChemistry, Vol. 37, No. 11 (1988), pp. 48-53). The "micro-emulsion" as used herein refers to a "micro-emulsion in the narrow sense," i.e., a thermodynamically stable isotropic single liquid phase.

The micro-emulsion refers to either one state of an O/W (oil-in-water) type microemulsion in which oil is solubilized by micelles, a W/O (water-in-oil) type microemulsion in which water is solubilized by reverse micelles, or a bicontinuous microemulsion in which the number of associations of surfactant molecules are rendered infinite so that both the aqueous phase and oil phase have a continuous structure.

The micro-emulsion may have a dispersed phase with a number average diameter of 100 nm or less, preferably 50 nm or less, and more preferably 20 nm or less, measured by laser granulometry.

The "nano-emulsion" here means an emulsion characterized by a dispersed phase with a size of less than 350 nm, the dispersed phase being stabilized by a crown of the (b) polyglyceryl fatty acid ester and the like that may optionally form a liquid crystal phase of lamellar type, at the dispersed phase/continuous phase interface. In the absence of specific opacifiers, the transparency of the nano-emulsions arises from the small size of the dispersed phase, this small size being obtained by virtue of the use of mechanical energy and especially a high-pressure homogenizer.

Nanoemulsions can be distinguished from microemulsions by their structure. Specifically, micro-emulsions are thermodynamically stable dispersions formed from, for example, micelles which are formed by the (b) polyglyceryl fatty acid ester and the like and swollen with the (a) oil. Furthermore, microemulsions do not require substantial mechanical energy in order to be prepared.

The micro-emulsion may have a dispersed phase with a number average diameter of 300 nm or less, preferably 200 nm or less, and more preferably 100 nm or less, measured by laser granulometry.

The cosmetic composition according to the present invention may be in the form of an O/W nano- or micro-emulsion, a W/O nano- or micro-emulsion or a bicontinuous emulsion.

It is preferable that the cosmetic composition according to the present invention be in the form of an O/W nano- or micro-emulsion.

It is preferable that the cosmetic composition according to the present invention be in the form of an O/W emulsion, and the (a) oil be in the form of a droplet with a number average particle size of 300 nm or less, preferably from 10 nm to 150 nm, and more preferably 20 nm to 140 nm.

The cosmetic composition according to the present invention can have a transparent or slightly translucent appearance, preferably a transparent appearance.

The transparency may be measured by measuring the nephelometric turbidity (for example, with 2100Q Portable Turbidimeter from HACH). The nephelometric turbidity of the cosmetic composition according to the present invention can be below 150 NTU (translucent), preferably below 100 NTU, more preferably below 50 NTU (transparent).

[Process and Use]

The cosmetic composition according to the present invention can be used for a non-therapeutic process, such as a cosmetic process, for treating the skin, the hair, mucous membranes, the nails, the eyelashes, the eyebrows and/or the scalp, by being applied to the skin, the hair, mucous membranes, the nails, the eyelashes, the eyebrows or the scalp.

The present invention also relates to a use of the cosmetic composition according to the present invention, as it is or in care products and/or washing products and/or make-up products and/or make-up-removing products for body and/or facial skin and/or mucous membranes and/or the scalp and/or the hair and/or the nails and/or the eyelashes and/or the eyebrows.

In other words, the cosmetic composition according to the present invention can be used, as it is, as the above product. Alternatively, the cosmetic composition according to the present invention can be used as an element of the above product. For example the cosmetic composition according to the present invention can be added to or combined with any other elements to form the above product.

The care product may be a lotion, a cream, a hair tonic, a hair conditioner, a sun screening agent, and the like. The washing product may be a shampoo, a face wash, a hand wash and the like. The make-up product may be a foundation, a mascara, a lipstick, a lip gloss, a blusher, an eye shadow, a nail varnish, and the like. The make-up-removing product may be a make-up cleansing agent and the like.

EXAMPLES

The present invention will be described in more detail by way of examples, which however should not be constructed as limiting the scope of the present invention.

Example 1 and Comparative Example 1

The following compositions according to Example 1 and Comparative Example 1, shown in Table 1, were prepared by mixing the components shown in Table 1 as follows: (1) mixing isopropyl myristate and polyglyceryl-5 laurate or PEG-20 triisostearate to form an oil phase; (2) heating the oil phase up to around 60° C.; (3) adding water into 25% of the oil phase followed by mixing to form Part 1; (4) mixing the remaining ingredients and the remaining oil phase followed by mixing to form Part 2; and (5) adding Part 1 to Part 2 followed by heating up to around 60° C. and mixing to obtain an O/W emulsion. The numerical values for the amounts of the components shown in Table 1 are all based on "% by weight" as active raw materials.

TABLE 1

| | Example 1 | Comparative Example 1 |
| --- | --- | --- |
| Lauryl glycoside | 7.7% | 7.7% |
| Disodium cocoyl glutamate | 2.5% | 2.5% |
| Cocobetaine | 2.3% | 2.3% |
| Isopropyl myristate | 5.0% | 5.0% |
| Glycerine | 5.0% | 5.0% |
| Sorbitol | 10.0% | 10.0% |
| Propandiol | 5.0% | 5.0% |
| Glyceryl caprylate | 0.5% | 0.5% |
| PG5 laurate* | 2.5% | — |
| PEG-20 triisostearate** | — | 2.5% |
| Citric acid | 0.23% | 0.23% |
| Water | q.s. | q.s. |
| pH | 7 | 7 |

*SUNSOFT A-121E (Taiyo Kagaku)
**EMALEX GWIS-320EX (NIHON EMULSION)

The aspect, stability and form quality of the obtained O/W emulsions according to Example 1 and Comparative Example 1 were determined as follows.

(Aspect)

The aspect of the composition was determined visually as follows.
1. Transparent (same as water)
2. Translucent (between 1 and 2)
3. Turbid (white)

(Stability)

The stability of the composition was determined after stocking 1 day at 4° C., RT (room temperature), and 45° C., as follows.
1. Stable: appearance did not change at all temperature;
2. Unstable: the formula became whiter or separated at least one temperature.

(Foam Quality)

The foam quality was measured by placing the composition through a foaming pump (Daiwa can F5), and the foam aspect was determined visually, as follows.
1. Good: homogeneous fine foam
2. Poor: heterogeneous foam having big bubbles The results are shown in Table 2.

TABLE 2

| | Example 1 | Comparative Example 1 |
| --- | --- | --- |
| Aspect | 1. Transparent | 3. Turbid |
| Stability | 1. Stable | 2. Unstable |
| Foam Quality | 1. Good | 2. Poor |

As is clear from the above results, it was found that the cosmetic composition in the form of an O/W emulsion according to the present invention had better aspects, stability and foam quality, which indicated that the O/W emulsion according to the present invention included smaller oil droplets.

Example 2 and Comparative Example 2

The following compositions according to Example 2 and Comparative Example 2, shown in Table 3, were prepared by mixing the components shown in Table 3 as follows: (1) mixing isopropyl myristate and polyglyceryl-5 laurate or PEG-20 triisostearate to form an oil phase; (2) heating the oil phase up to around 60° C.; (3) adding water into 25% of the oil phase followed by mixing to form Part 1; (4) mixing the remaining ingredients and the remaining oil phase followed by mixing to form Part 2; and (5) adding Part 1 to Part 2 followed by heating up to around 60° C. and mixing to obtain an O/W emulsion. The numerical values for the amounts of the components shown in Table 3 are all based on "% by weight" as active raw materials.

TABLE 3

|  | Example 2 | Comparative Example 2 |
|---|---|---|
| Lauryl glycoside | 3.0% | 3.0% |
| Sodium amilite | 5.4% | 5.4% |
| Cocobetaine | 3.6% | 3.6% |
| Isopropyl myristate | 3.0% | 3.0% |
| Glycerine | 5.0% | 5.0% |
| Propandiol | 5.0% | 5.0% |
| Glyceryl caprylate | 0.5% | 0.5% |
| PG5 laurate* | 1.5% | — |
| PEG-20 triisostearate** | — | 1.5% |
| Citric acid | 0.23% | 0.23% |
| Water | q.s. | q.s. |
| pH | 6.5 | 6.5 |

*SUNSOFT A-121E (Taiyo Kagaku)
**EMALEX GWIS-320EX (NIHON EMULSION)

The aspect, stability and form quality of the obtained O/W emulsions according to Example 2 and Comparative Example 2, were determined as explained above. The results are shown in Table 4.

TABLE 4

|  | Example 2 | Comparative Example 2 |
|---|---|---|
| Aspect | 1-Transparent | 2-Translucent |
| Stability | 1-Stable | 2-Unstable |
| Foam quality | 1-Good | 2-Poor |

As is clear from the above results, it was found that the cosmetic composition in the form of an O/W emulsion according to the present invention had better aspects, stability and foam quality, which indicated that the O/W emulsion according to the present invention included smaller oil droplets.

Example 3 and Comparative Example 3

The following compositions according to Example 3 and Comparative Example 3, shown in Table 5, were prepared by mixing the components shown in Table 5 as follows: (1) mixing isopropyl myristate and polyglyceryl-5 laurate or PEG-20 triisostearate to form an oil phase; (2) heating the oil phase up to around 60° C.; (3) adding water into 25% of the oil phase followed by mixing to form Part 1; (4) mixing the remaining ingredients and the remaining oil phase followed by mixing to form Part 2; and (5) adding Part 1 to Part 2 followed by heating up to around 60° C. and mixing to obtain an O/W emulsion. The numerical values for the amounts of the components shown in Table 5 are all based on "% by weight" as active raw materials.

TABLE 5

|  | Example 3 | Comparative Example 3 |
|---|---|---|
| Lauryl glycoside | 3.0% | 3.0% |
| Disodium cocoyl glutamate | 2.0% | 2.0% |
| Cocobetaine | 4.0% | 4.0% |
| Isopropyl myristate | 1.0% | 1.0% |
| Glycerine | 5.0% | 5.0% |
| Propandiol | 5.0% | 5.0% |

TABLE 5-continued

|  | Example 3 | Comparative Example 3 |
|---|---|---|
| Glyceryl caprylate | 0.5% | 0.5% |
| PG5 laurate* | 0.5% | — |
| PEG-20 triisostearate** | — | 0.5% |
| Citric acid | 0.12% | 0.12% |
| Water | q.s. | q.s. |
| pH | 6.5 | 6.5 |

*SUNSOFT A-121E (Taiyo Kagaku)
**EMALEX GWIS-320EX (NIHON EMULSION)

The aspect, stability and form quality of the obtained O/W emulsions according to Example 3 and Comparative Example 3, were determined as explained above. The results are shown in Table 6.

TABLE 6

|  | Example 3 | Comparative Example 3 |
|---|---|---|
| Aspect | 1-Transparent | 2-Translucent |
| Stability | 1-Stable | 2-Unstable |
| Foam quality | 1-Good | 2-Poor |

As is clear from the above results, it was found that the cosmetic composition in the form of an O/W emulsion according to the present invention had better aspects, stability and foam quality, which indicated that the O/W emulsion according to the present invention included smaller oil droplets.

Examples 4 and 5

The following compositions according to Examples 4 and 5, shown in Table 7, were prepared by mixing the components shown in Table 7 as follows: (1) mixing isopropyl myristate and polyglyceryl-5 laurate to form an oil phase; (2) heating the oil phase up to around 60° C.; (3) adding water into 25% of the oil phase followed by mixing to form Part 1; (4) mixing the remaining ingredients and the remaining oil phase followed by mixing to form Part 2; and (5) adding Part 1 to Part 2 followed by heating up to around 60° C. and mixing to obtain an O/W emulsion. The numerical values for the amounts of the components shown in Table 7 are all based on "% by weight" as active raw materials.

TABLE 7

|  | Example 4 | Example 5 |
|---|---|---|
| Lauryl glycoside[1] | 7.7% | — |
| Decyl glucoside[3] | — | 7.7% |
| Disodium cocoyl glutamate | 2.5% | 2.5% |
| Cocobetaine | 2.3% | 2.3% |
| Isopropyl myristate | 5.0% | 5.0% |
| Glycerine | 5.0% | 5.0% |
| Sorbitol | 10.0% | 10.0% |
| PG5 laurate* | 2.5% | 2.5% |
| Citric acid | 0.23% | 0.23% |
| Water | q.s. | q.s. |
| pH | 6.5 | 6.5 |

[1]PLANTAREN 1200N UP (Cognis)
[3]PLANTACARE 2000 UP (Cognis)
*SUNSOFT A-121E (Taiyo Kagaku)

| Chemical name | Supplier | | C8 | C10 | C12 | C14 | C16 |
|---|---|---|---|---|---|---|---|
| Plantacare 200 UP | COGNIS | decyl glucoside | 33-40 | 21-28 | 27-32 | 9-12 | — |
| Plantaren 1200 N UP | COGNIS | lauryl glucoside | — | — | 65-75 | 22-28 | 4-8 |

The aspect, stability and form quality of the obtained O/W emulsions according to Example 4 and Example 5, were determined as explained above. The results are shown in Table 8.

TABLE 8

| | Example 4 | Example 5 |
|---|---|---|
| Aspect | 1-Transparent | 2-Translucent |
| Stability | 1-Stable | 1-Stable |
| Foam quality | 1-Good | 1-Good |

Here, Examples 4 and 5 showed both good stability and good foam, but Example 4 is preferred because it was more transparent.

The invention claimed is:

1. A foaming composition in the form of a nano or micro-emulsion comprising:
   (a) at least one oil;
   (b) at least one polyglyceryl fatty acid ester having an HLB value of from 9.0 to 14.0;
   (c) at least one $C_{6-30}$ alkyl (poly)glucoside type surfactant;
   (d) at least one amphoteric surfactant; and
   (e) water.

2. The cosmetic composition according to claim 1, wherein the at least one oil is chosen from oils of plant or animal origin, synthetic oils, silicone oils, hydrocarbon oils, hydrocarbon oils which are in the form of a liquid at room temperature, or mixtures thereof.

3. The cosmetic composition according to claim 1, wherein the at least one oil is chosen from oils having a molecular weight below about 600 g/mol.

4. The cosmetic composition according to claim 1, wherein the total amount of the oil ranges from about 0.1% to about 30% by weight, relative to the total weight of the composition.

5. The cosmetic composition according to claim 1, wherein the at least one polyglyceryl fatty acid ester has an HLB value ranging from about 10.0 to 14.0.

6. The cosmetic composition according to claim 1, wherein the at least one polyglyceryl fatty acid ester has a polyglyceryl moiety derived from 2-10 glycerins.

7. The cosmetic composition according to claim 1, wherein the at least one polyglyceryl fatty acid ester is chosen from the mono, di, or tri esters of lauric acid; the mono, di, or tri esters of isostearic acid; the mono, di, or tri esters of oleic acid; or mixtures thereof.

8. The cosmetic composition according to claim 7, wherein the at least one polyglyceryl fatty acid ester is chosen from PG2 isostearate, PG2 laurate, PG2 caprate, PG-5 laurate, PG-4 laurate, PG-5 oleate, and PG-5 dioleate, PG5 myristate, PG5 trioleate, PG5 stearate, PG5 isostearate, PG5 triisostearate, PG10 trilaurate, PG10 isostearate, PG10 diisostearate, PG10 oleate, PG10 trioleate, PG10 triisostearate; a mixture of polyglyceryl fatty acid esters, a mixture of polyglyceryl fatty acid esters having a polyglyceryl moiety derived from 3 to 6 glycerins, a mixture of polyglyceryl fatty acid esters having a polyglyceryl moiety derived from 4 to 6 glycerins; a mixture comprising at least about 30% by weight of a polyglyceryl fatty acid ester with a polyglyceryl moiety consisting of 4, 5 or 6 glycerins; or mixtures thereof.

9. The cosmetic composition according to claim 1, wherein the at least one polyglyceryl fatty acid ester raw material comprises an ester of a fatty acid and polyglycerine chosen from esters of a fatty acid and polyglycerine containing about 70% or more of polyglycerine whose polymerization degree is 4 or more, esters of a fatty acid and polyglycerine containing equal to or more than about 60% of polyglycerine whose polymerization degree is between 4 and 11, esters of a fatty acid and polyglycerine containing equal to or more than about 30% of polyglycerine whose polymerization degree is 5, or mixtures thereof.

10. The cosmetic composition according to claim 1, wherein the total amount of the polyglyceryl fatty acid ester ranges from about 0.1% to about 15% by weight, relative to the total weight of the composition.

11. The cosmetic composition according to claim 1, wherein the weight ratio of the total amount of the polyglyceryl fatty acid ester to the total amount of the oil ranges from about 0.3 to about 6.

12. The cosmetic composition according to claim 1, wherein the at least one alkyl (poly)glucoside type surfactant is represented by the formula:

$$R_1O\text{---}(R_2O)_t\text{-}(G)_v$$

wherein:
   $R_1$ represents a linear or branched $C_1$-$C_{30}$ alkyl and/or alkylene radical, or an aralkyl radical, the linear or branched aralkyl radical of which comprises from 7 to 30 carbon atoms,
   $R_2$ represents at least one alkylene radical comprising approximately from 2 to 4 carbon atoms,
   G represents a sugar unit comprising from 5 to 6 carbon atoms,
   t denotes a value ranging from 0 to 10, and
   v denotes a value ranging from 1 to 15.

13. The cosmetic composition according to claim 1, wherein the at least one $C_{6-30}$ alkyl (poly)glucoside type surfactant comprises lauryl glucoside.

14. The cosmetic composition according to claim 1, wherein the total amount of alkyl (poly)glucoside type surfactant ranges from about 0.1 to about 25% by weight, relative to the total weight of the composition.

15. The cosmetic composition according to claim 1, wherein the at least one amphoteric surfactant is chosen from alkylbetaines, amidoaminecarboxylated derivatives, sultaine, alkyl amphoacetate derivatives, or mixtures thereof.

16. The cosmetic composition according to claim 1, wherein the total amount of amphoteric surfactant ranges from about 0.1 to about 25% by weight, relative to the total weight of the composition.

17. The cosmetic composition according to claim 1, further comprising at least one additional component chosen from anionic surfactants, polyols, thickening agents, associative thickeners, or mixtures thereof.

18. The cosmetic composition according to claim 1,
wherein the cosmetic composition is in the form of an O/W emulsion, and
wherein the at least one oil is in the form of a droplet having a number average particle size of about 300 nm or less.

19. The cosmetic composition according to claim 1, wherein the cosmetic composition has a nephelometric turbidity lower than about 150 TU.

20. A non-therapeutic method for treating the skin, the hair, mucous membranes, the nails, the eyelashes, the eyebrows, and/or the scalp, the method comprising:
applying to the skin, the hair, mucous membranes, the nails, the eyelashes, the eyebrows, and/or the scalp a foaming composition in the form of a nano or microemulsion comprising:
(a) at least one oil;
(b) at least one polyglyceryl fatty acid ester having an HLB value of from 9.0 to 14.0;
(c) at least one $C_{6-30}$ alkyl (poly)glucoside type surfactant;
(d) at least one amphoteric surfactant; and
(e) water.

* * * * *